(12) United States Patent
Lederman et al.

(10) Patent No.: US 12,156,864 B2
(45) Date of Patent: Dec. 3, 2024

(54) ANALOGS OF CYCLOBENZAPRINE AND AMITRYPTILENE

(71) Applicant: TONIX PHARMACEUTICALS HOLDING CORP, New York, NY (US)

(72) Inventors: Seth Lederman, New York, NY (US); Darryl Rideout, Milford, PA (US); Greg Sullivan, New York, NY (US)

(73) Assignee: TONIX PHARMACEUTICALS HOLDING CORP, New York, NY (US)

( * ) Notice: Subject to any disclaimer, the term of this patent is extended or adjusted under 35 U.S.C. 154(b) by 0 days.

(21) Appl. No.: 18/075,386

(22) Filed: Dec. 5, 2022

(65) Prior Publication Data

US 2023/0149348 A1    May 18, 2023

Related U.S. Application Data

(62) Division of application No. 16/630,832, filed as application No. PCT/US2018/042184 on Jul. 13, 2018, now Pat. No. 11,517,557.

(60) Provisional application No. 62/532,353, filed on Jul. 13, 2017.

(51) Int. Cl.
| | | |
|---|---|---|
| *A61K 31/397* | (2006.01) | |
| *A61K 31/135* | (2006.01) | |
| *A61K 45/06* | (2006.01) | |
| *C07C 211/32* | (2006.01) | |
| *C07D 205/04* | (2006.01) | |

(52) U.S. Cl.
CPC .......... *A61K 31/397* (2013.01); *A61K 31/135* (2013.01); *A61K 45/06* (2013.01); *C07C 211/32* (2013.01); *C07D 205/04* (2013.01)

(58) Field of Classification Search
CPC .... A61K 31/397; A61K 31/135; A61K 45/06; C07C 211/32; C07D 205/04
USPC ..................................................... 514/210.01
See application file for complete search history.

(56) References Cited

U.S. PATENT DOCUMENTS

| | | |
|---|---|---|
| 3,454,643 A | 7/1969 | Cope |
| 4,861,862 A | 8/1989 | Tyrell |
| 5,073,543 A | 12/1991 | Marshall et al. |
| 5,120,548 A | 6/1992 | McClelland et al. |
| 5,354,566 A | 10/1994 | Addesso et al. |
| 5,591,767 A | 1/1997 | Mohr et al. |
| 5,595,989 A | 1/1997 | Andersen et al. |
| 5,639,476 A | 6/1997 | Oshlack et al. |
| 5,674,533 A | 10/1997 | Santus et al. |
| 5,733,566 A | 3/1998 | Lewis |
| 5,741,791 A | 4/1998 | Olsen |
| 6,248,363 B1 | 6/2001 | Patel et al. |
| 6,267,985 B1 | 7/2001 | Chen et al. |
| 6,309,663 B1 | 10/2001 | Patel et al. |
| 6,358,944 B1 | 3/2002 | Lederman et al. |
| 6,383,471 B1 | 5/2002 | Chen et al. |
| 6,395,788 B1 | 5/2002 | Iglehart |
| 6,720,001 B2 | 4/2004 | Chen et al. |
| 6,761,903 B2 | 7/2004 | Chen et al. |
| 2006/0281722 A1 | 12/2006 | Foley et al. |
| 2010/0105778 A1 | 4/2010 | Kranzler |
| 2015/0111966 A1 | 4/2015 | Kandula |
| 2017/0065538 A1 | 3/2017 | Lederman et al. |

FOREIGN PATENT DOCUMENTS

| | | |
|---|---|---|
| GB | 1274261 A | 5/1972 |
| JP | S49-039675 A | 10/1974 |
| JP | H10-508308 A | 8/1998 |
| JP | 2009523734 A | 6/2009 |
| JP | 2015-519404 A | 9/2015 |
| WO | 2006088786 A2 | 8/2006 |
| WO | 2009064493 A1 | 5/2009 |
| WO | 2010035047 A1 | 4/2010 |
| WO | 2012079017 A1 | 6/2012 |
| WO | 2012098563 A2 | 7/2012 |

OTHER PUBLICATIONS

Sep. 2, 2022 Office Action issued in Chinese Application No. 2018800507582.
European application No. 18831505, European Examination Report mailed Mar. 11, 2022, 7 pages.
European application No. 18831505, Extended European Search Report mailed Feb. 15, 2021, 11 pages.
Zkang et al., "Formation of Mammalian of Metabolites of Cyclobenzaprine by the Fungus, Cunninghamella Elegans", hemico-Biological Interactions, vol. 102, 1996, pp. 79-92.
Breyer-Pfaff et al., "Phenolic Metabolites of Amitriptyline and Nortriptyline in Rat Bile", Ding Metabolism and Disposition, vol. 15, No. 6, 1987, pp. 882-889.
Balant, Prodrugs for the improvement of ding absorption via different routes of administration. Eur J Ding Metab Pharmacokinet. Apr.-Jun. 1990;15(2).143-153.
Bartnik and Marchand, Synthesis and Chemistry of Substituted 1-Azabicyclo[1.1.0]butanes. Synlett 1997.1029-1039.
Boehm, Statistical Review and Evaluation. Zoloft (Sertraline HCI). sNDA#19-839 and 20-990 FDA; Sep. 3, 2003. NDA No. 1-32.
Engelhardt et al., Antidepressants. Tetrabenazine-Antagonizing Activity in a Series of 5H-Dibenzo[a,d] cycloheptene-5-propylamines. J Med Chem. Mar. 1968; 11(2).325-332.
Jornada et al., The Prodrug Approach. A Successful Tool for Improving Drug Solubility. Molecules. Dec. 29, 2015;21(1).42 (31 pages).
Kamata et al., Efficient Heterogeneous Oxidation of Alkylarenes with Molecular Oxygen. Org Lett. Sep. 30, 2004;6(20).3577-3580.
Karki et al., Mechanism of Oxidative Amine Dealkylation of Substituted N,N-Dimethylanilines by Cytochrome P-450. Application of Isotope Effect Profiles. J Am Chem Soc. Apr. 1995;117(13). 3657-3664.

(Continued)

*Primary Examiner* — Kristin A Vajda
(74) *Attorney, Agent, or Firm* — Think IP, P.C.

(57) ABSTRACT

The present invention relates to cyclobenzaprine analogs and amitriptyline analogs, including deuterated forms useful for treatment or prevention of symptoms associated with post-traumatic stress disorder.

14 Claims, 2 Drawing Sheets

(56) References Cited

OTHER PUBLICATIONS

Katz and Dube, Cyclobenzaprine in the Treatment of Acute Muscle Spasm. Review of a Decade of Clinical Experience. Clin Ther. 1988;10(2).216-228.
Lawrence, Statistical Review and Evaluation. Zoloft (Sertraline HCI). sNDA#19-839/S-035 and 20-990 FDA; May 31, 2000. pp. 1-9.
Najjar and Karaman, The prodrug approach in the era of drug design. Expert Opin Ding Deliv. Jan. 2019;16(1).1-5.
Parajuli et al., Prodrug as a Novel Approach of Drug Delivery—A Review. J Drug Deliv Ther. 2015;5(3).5-9.
Pubchem CID 49849594, 3-(Dibenzo[1,2-a.1',2'-e][7]annulen-11-ylidene)-N,N-bis(trideuteriomethyl)propan-1-amine. Feb. 1, 2011. Accessed online at . https://pubchem.ncbi.mm.nih.gov/compound/49849594#section=Identification-and-Related-Records.
Pubchem SID 313054526, Bromocyclopropane D4. Apr. 28, 2016. Accessed online at https://pubchem.ncbi.mm.nih.gov/substance/313054526.
Pubchem SID 347228897, Bromocyclopropane-2,2,3,3-D4. Oct. 20, 2017 accessed online at https://pubchem.ncbi.nlm.nih.gov/substance/347228897#section=Extemal-ID.
Pubchem SID 349658512, 1398065-55-8. Dec. 18, 2017. Accessed online at https://pubchem.ncbi.mm.nih.gov/substance/349658512.
Pubchem SID 355151531, 1398065-55-8. Mar. 27, 2018. Accessed online at https://pubchem.ncbi.mm.nih.gov/substance/35515153&\.
Rothbaum et al., A pooled analysis of gender and trauma-type effects on responsiveness to treatment of PTSD with menlafaxine extended release or placebo. J Clin Psychiatry. Oct. 2008; 69(10). 1529-1539.
Sakai et al., Chemoselective Isomerization of Secondary-Type Propargylic Alcohols to Propargylic/Allenic Bromides, and Brominated Dienes with Appel-Type Reaction Conditions. Synlett, 2009, 2105-2106.
Singh and Shreeve, Nucleophilic fluorination of amino alcohols and diols using Deoxofluor. J Fluorine Chemistry Jul. 2002;116(1).23-26.
Toronto Research Chemicals, B682763—Bromocyclopropane-d5. Catalog listing. Accessed online at https://www.trc-canada.com/product-detail/?B682763 on Dec. 31, 2020.
Wang et al., Practical in situ-generation of phosphinite ligands for palladium-catalyzed carbonylation of (hetero)aryl promides forming esters. Chem Commun (Camb). Jul. 4, 2017;53(54).7469-7472.
Zolotarev et al., Ligands of Glutamate and Dopamine Receptors Evenly Labeled with Hydrogen Isotopes. Russian J Bioorg Chem. 2009;35(3).296-305.
Blake et al., The Development of a Clinician-Administered PTSD Scale. J Trauma Stress. Jan. 1995;8(1).75-90.
Daugherty et al., Serotonin Receptor Profiles of Bedtime Pharmacotherapies Targeting Post-traumatic Stress Disorder (PTSD). Society of Biological Psychiatry Annual Meeting. May 2015. Abstract 728 (1 page).
Friedman et al., Randomized, Double-Blind Comparison of Sertraline and Placebo for Posttraumatic Stress Disorder in a Department of Veterans Affairs Setting. J Clin Psychiatry. May 2007;68(5).711-720.
Group TMoP-TSW, The Office of Quality and Performance V, Washington, DC, Quality Management Division USAM.VA;DoD Clinical Practice Guideline. Management of Post-Traumatic Stress. In. Affairs Do V, Defense Do, eds; 2010 (253 pages).
Hoge et al., Combat duty in Iraq and Afghanistan, Mental Health Problems, and Barriers to Care. N Engl J Med. Jul. 1, 2004;351(1). 13-22.
Liang et al., Modified Palladium-Catalyzed Sonogashira Cross-Coupling Reactions under Copper-, Amine-, and Solvent-Free Conditions. J Org Chem. Jan. 6, 2006;71(1).379-381.
Noda et al., Synthesis of 5-(((R,S)-5-((9-Fluorenylmethoxycarbonyl)amino)-10, 11-dihydrodibenzo[a,d]cyclohepten-2-yl)oxy)valeric Acid (CHA) and 5-(((R,S)-5-((9-Fluorenylmethoxycarbonyl)amino)dibenzo[a,d]cyclohepten-2-yl)oxy) valeric Acid (CHE) Handles for the Solid-Phase Synthesis of C-Terminal Peptide Amides under Mild Conditions. J Org Chem. 1994;59(26).7968-7975.
Ramsawh et al., Risk for suicidal behaviors associated with PTSD, depression, and their comorbidity in the US Army. J Affect Disord. Jun. 2014;161.116-122.
Shang et al., Iron-Catalyzed Ortho C—H Methylation of Aromatics Bearing a Simple Carbonyl Group with Methylaluminum and Tridentate Phosphine Ligand. J Am Chem Soc. Aug. 17, 2016;138(32). 10132-10135.
Statistical Review and Evaluation. Zoloft (Sertraline HCl). NDA No. 19-839 . Received Dec. 28, 1998.25 pages.
Thomas et al., Prevalence of Mental Health Problems and Functional Impairment Among Active Component and National Guard Soldiers 3 and 12 Months Following Combat in Iraq. Arch Gen Psychiatry. Jun. 2010;67(6).614-623.
Umeda et al., Synthesis of Isocoumarins. Rhenium Complex-Catalyzed Cyclization of 2-Ethynylbenzoic Acids. Heterocycles Oct. 2015;91(11).2172-2179—Engl abstract only.
Weaver et al., An Instrument to Measure Functional Status Outcomes for Disorders of Excessive Sleepiness. Sleep. Oct. 1997;20(10). 835-843.
Yoshida et al., MexAB-OprM specific efflux pump inhibitors in Pseudomonas aeruginosa. Part 6. exploration of aromatic substituents. Bioorg Med Chem. Dec. 15, 2006;14(24).8506-8518.
International Search Report and written Opinion issued in PCT/US18/42184 dated Nov. 5, 2018 (9 pages).
International Preliminary Report on Patentability issued in PCT/US18/42184 dated Jan. 14, 2020 (6 pages).
Pubchem. CID 2895, Cyclobenzaprine. Mar. 25, 2005, pp. 1-8. Retrieved from the Internet <URL. https.//pubchem.ncbi.mm.nih.gov/compound/2895>.
Feb. 7, 2023 Second Office Action issued in Japanese Application No. 2020-523238.
Decision of Refusal dated Oct. 27, 2023 issued in Japanese Application No. 2020-523238.
Rejection Decision dated Nov. 27, 2023 issued in Chinese Application No. 2018800507582.
Examination Report dated Jun. 27, 2023 issued in European Patent Application No. 18831505.5.

ANALOGS OF CYCLOBENZAPRINE AND AMITRYPTILENE

RELATED APPLICATIONS

This application claims priority to and the benefit of U.S. Ser. No. 16/630,832, filed on Jan. 31, 2020 which is a 35 U.S.C. 371 of International Application No. PCT/US2018/042184, filed Jul. 13, 2018, which claims priority to and the benefit of U.S. Application No. 62/532,353, filed Jul. 13, 2017, the disclosures of which are hereby incorporated herein by reference in their entireties.

FIELD OF THE INVENTION

The present invention relates to new analogs of cyclobenzaprine. The new analogs have similar pharmacodynamic properties as cyclobenzaprine and can be used to treat the same conditions as cyclobenzaprine, such as muscle spasms, fibromyalgia syndrome, traumatic brain injury, sleep issues and post-traumatic stress syndrome (PTSD) including the sleep issues associated with that disorder.

BACKGROUND OF THE DISCLOSURE

Cyclobenzaprine, or 3-(5H-dibenzo[a,d]cyclohepten-5-ylidene)-N,N-dimethyl-1-propanamine, was first approved by the U.S. Food and Drug Administration in 1977 for the treatment of acute muscle spasms of local origin. (Katz, W., et al., Cyclobenzaprine in the Treatment of Acute Muscle Spasm: Review of a Decade of Clinical Experience, *Clinical Therapeutics* 10:216-228 (1988)). Cyclobenzaprine has also been studied in the treatment of fibromyalgia. In a study of 120 fibromyalgia patients, those receiving cyclobenzaprine (10 to 40 mg) over a 12-week period had significantly improved quality of sleep and pain score. There was also a reduction in the total number of tender points and muscle tightness.

The utility of a very low dose cyclobenzaprine as an agent for improving the quality of sleep, as a sleep deepener, or for treating sleep disturbances has been investigated. The very low dosage regimen was viewed as particularly useful in treating sleep disturbances caused by, exacerbated by or associated with fibromyalgia syndrome, prolonged fatigue, chronic fatigue, chronic fatigue syndrome, a sleep disorder, a psychogenic pain disorder, chronic pain syndrome (type II), the administration of a drug, autoimmune disease, stress or anxiety or for treating an illness caused by or exacerbated by sleep disturbances, and symptoms of such illness and generalized anxiety disorder. See U.S. Pat. Nos. 6,395,788 and 6,358,944, incorporated by reference herein.

Posttraumatic stress disorder (PTSD) is one of the most prevalent and disabling psychiatric conditions afflicting US Warfighters previously deployed as part of Operation Enduring Freedom (OEF), Operation Iraqi Freedom (OIF), and Operation New Dawn (OND) (Thomas J L, et al., Prevalence of mental health problems and functional impairment among active component and National Guard soldiers 3 and 12 months following combat in Iraq. *Arch Gen Psychiatry.* 2010; 67(6):614-6231; and Hoge C W, et al., Combat duty in Iraq and Afghanistan, mental health problems, and barriers to care. *N Engl J Med.* 2004; 351(1):13-22.) Of the approximately 20 veteran suicides each day, an unknown but significant number are associated with either untreated or inadequately treated PTSD. Among service members with PTSD, the rate of past year suicidal ideation or attempts was 18% in a 2014 report from the Army Study to Assess Risk and Resilience in Service Members, or STARRS study. (Ramsawh H J, et al., Risk for suicidal behaviors associated with PTSD, depression, and their comorbidity in the US Army. *Journal of affective disorders.* 2014; 161:116-122). Only two pharmacotherapies, sertraline and paroxetine, both selective serotonin reuptake inhibitors (SSRIs), are FDA-approved for PTSD. Sertraline failed to show efficacy in veterans (Friedman M J, et al., Randomized, double-blind comparison of sertraline and placebo for posttraumatic stress disorder in a Department of Veterans Affairs setting. *J Clin Psychiatry.* 2007; 68(5):711-720) and males (Smith D. Statistical Review and Evaluation: Zoloft (*Sertraline HCl*): FDA; Sep. 27 1999. NDA Number: 19-839) with PTSD; paroxetine was never studied in a predominantly military-related PTSD population. The serotonin-norepinephrine reuptake inhibitor (SNRI), venlafaxine ER, also had no effect on PTSD or disability in the combat subsample (N=77) of a pooled analysis. (Rothbaum B O, et al.) A pooled analysis of gender and trauma-type effects on responsiveness to treatment of PTSD with venlafaxine extended release or placebo. *J Clin Psychiatry.* 2008; 69(10):1529-1539). In addition, there is no published report of any pharmaceutical agent that has been successful in a large multicenter trial for the treatment of a sample with PTSD that is predominantly military-related. Despite this lack of evidence-based pharmacotherapy treatments in military-related PTSD, VA treatment guidelines offer only the SSRIs and SNRIs as recommended first-line pharmacotherapies due to "good evidence . . . that the intervention improves important health outcomes". (Group TMoP-TSW, The Office of Quality and Performance V, Washington, DC, Quality Management Division USAM. VA/DoD Clinical Practice Guideline: Management of Post-Traumatic Stress. *In: Affairs DoV, Defense Do*, eds; 2010). These findings place focus on the critical lack of evidence-based somatic treatments for military-related PTSD and highlight the urgent, and as yet unmet, need for novel pharmaceutical approaches operating through distinct mechanisms of action from currently approved or recommended products for military-related PTSD.

For the past several years, Applicant has been making substantial progress in the development of TNX-102 SL, a proprietary sublingual formulation of the tricyclic molecule cyclobenzaprine, for the treatment of PTSD. Cyclobenzaprine has high affinity binding and antagonist activity at three receptors with established roles in regulating sleep physiology, namely the serotonin-2A (5-HT2A), $\alpha_1$-adrenergic, and histaminergic$_1$ (H$_1$) receptors. (Daugherty B, Sullivan G, Gershell L, Lederman S. Serotonin Receptor Profiles of Bedtime Pharmacotherapies Targeting Post Traumatic Stress Disorder (PTSD). *Society of Biological Psychiatry Annual Meeting.* Vol 77; 2015:271S-272S). Due to emerging knowledge of the central role of sleep pathology in PTSD, Applicant hypothesized that selective targeting of these receptors during sleep hours with TNX-102 SL would improve sleep quality and consequently have anti-stress system (e.g., sympatholytic) effects and would be permissive to sleep-dependent processing of emotional memories (e.g., extinction consolidation) necessary for recovery from PTSD. To this end, Applicant developed an eutectic formulation of TNX-102 SL that rapidly delivers cyclobenzaprine to the circulation via sublingual administration. The unique composition of cyclobenzaprine, beta mannitol, and potassium phosphate dibasic within the TNX-102 SL tablet facilitates efficient transmucosal absorption resulting in a unique PK profile and reduced production of its long-lived, active metabolite, norCBP. In addition, the receptor affinities of the parent molecule are such that differing therapeutic effects can be achieved depending on the dynamics of the plasma concentration realized after bedtime dosing. The sleep and stress system benefits observed with the use of low doses of sublingual TNX-102 SL at bedtime differ from those expected with 15-30 mg of oral cyclobenzaprine, which is the current labeled daily usage of cyclobenzaprine as an adjunct to rest and physical therapy for muscle spasm.

In 2015, Applicant initiated and completed enrollment in a multicenter 12-week Phase 2 study of TNX-102 SL in military-related PTSD. Entry criteria required PTSD to have developed in relation to trauma(s) that occurred during military service since 2001, resulting in a sample with PTSD predominantly in response to combat traumas incurred during deployments in Operation Iraqi Freedom (OIF)/Operation Enduring Freedom (OEF)/Operation New Dawn (OND). A total of 245 participants were enrolled across 24 centers in the US, and results were reported in May, 2016. TNX-102 SL at 5.6 mg was demonstrated to be effective for treatment of PTSD, while treatment with 2.8 mg was suboptimal. The Clinician-Administered PTSD Scale for DSM-5 (CAPS-5) primary efficacy endpoint results were cross-validated by significant effects on key secondary measures of global and functional improvement. The hypothesized mechanism was supported by data demonstrating early (<2 weeks) and robust effects on sleep disturbance and hyperarousal, with progressive improvement in a wide array of PTSD symptoms continuing over the 12-weeks of treatment.

Disturbed sleep is a central feature of post-traumatic stress disorder (PTSD) that is included in two thirds of major symptom clusters in DSM-IV. Several observations suggest that disturbed sleep exacerbates or prolongs PTSD: (1) sleep disturbance in reaction to trauma is a marker for the development of PTSD; (2) the severity of established PTSD correlates with the severity of sleep disturbance; (3) sleep arousals and nightmares are core symptoms; and (4) at least one pharmacologic agent (prazosin) that targets the sleep disturbance in PTSD administered at bedtime not only improves sleep but also improves global clinical status. Thus, it is important to develop new methods and pharmaceutical compositions that will attenuate arousal signals that disrupt sleep, reduce PTSD nightmares and other measures of disturbed sleep, and improve PTSD global symptoms with minimal side effects.

SUMMARY OF THE INVENTION

Disclosed herein are cyclobenzaprine analogs of Formula A:

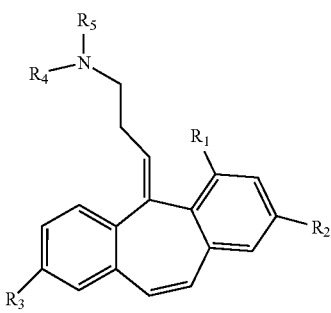

Formula A and pharmaceutically acceptable salts thereof. In some embodiments
$R_1$ is selected from H, $C_{1-4}$-alkyl, and $C_{1-4}$-alkoxy;
$R_2$ is selected from H, Br, $(CH_2)_nCO_2R$ where n=0 to 3 and
$R=C_{1-4}$-alkyl, $C_{1-4}$-alkoxy, and halogen;
$R_3$ is selected from H, $C_{1-4}$-alkoxy, OH, and OCOR where $R=C_{1-4}$-alkyl;
$R_4$ is $C_{1-4}$-alkyl wherein if $R_4$ is ethyl the terminus carbon can be optionally substituted by fluorine one to three times; and
$R_4$ and $R_5$ taken together form a 4-membered saturated ring substituted with 1 or more fluorines and optionally further substituted with methyl, methoxy, $CF_3$, or $CHF_2$.

In another embodiment, are amitriptyline analog compounds of Formula B

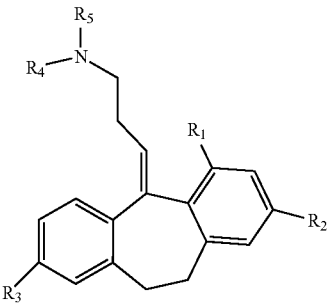

Formula B and pharmaceutically acceptable salts thereof wherein:
$R_1$ is selected from H, $C_{1-4}$-alkyl, and $C_{1-4}$-alkoxy;
$R_2$ is selected from H, Br, $(CH_2)_nCO_2R$ where n=0 to 3 and $R=C_{1-4}$-alkyl, $C_{1-4}$-alkoxy, and halogen;
$R_3$ is selected from H, $C_{1-4}$-alkoxy, OH, and OCOR where $R=C_{1-4}$-alkyl;
$R_4$ is $C_{1-4}$-alkyl wherein if $R_4$ is ethyl the terminus carbon can be optionally substituted by fluorine one to three times; and
$R_4$ and $R_5$ taken together form a 4-membered saturated ring substituted with 1 or more fluorines and optionally further substituted with methyl, methoxy, $CF_3$, or $CHF_2$.

DETAILED DESCRIPTION OF THE EMBODIMENTS

Figure 1:
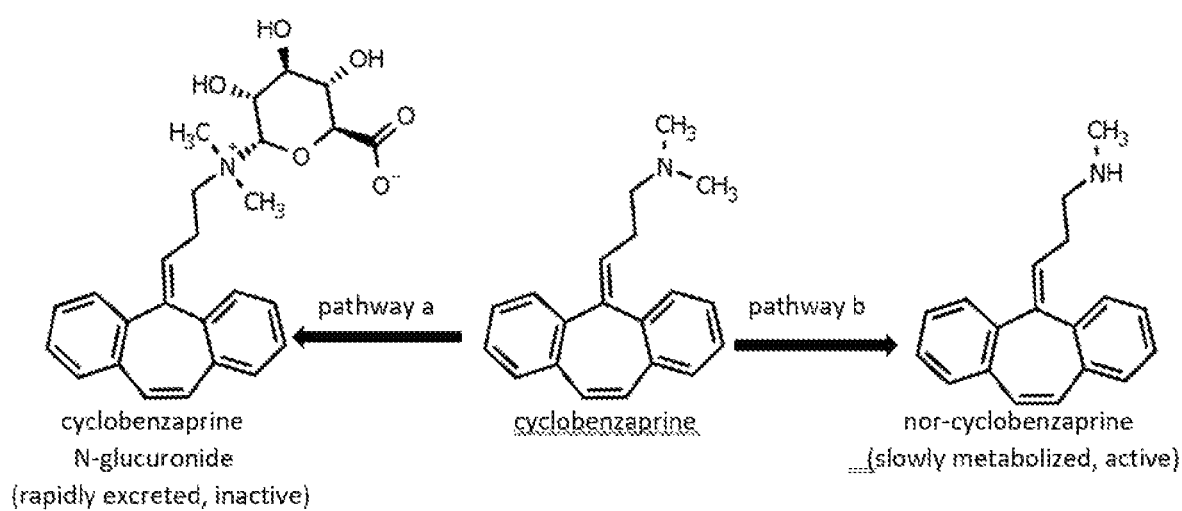
FIG. 1 shows the two metabolic pathways that breaks down cyclobenzaprine in humans

In humans, cyclobenzaprine breaks down rapidly by 2 metabolic pathways (FIG. 1).
The nor-cyclobenzaprine metabolite formed via pathway b (N-dealkylation) has a much longer half-life of ~48 hours. Patients treated with oral cyclobenzaprine at doses sufficient to treat PTSD-associated sleep disorders experience drowsiness the next day as a result of nor-cyclobenzaprine accumulation. Thus, an aspect disclosed herein are analogs of cyclobenzaprine (or a small molecule with similar pharmacodynamic properties) that cause little or no drowsiness by altering the metabolic properties of cyclobenzaprine.

Figure 2:
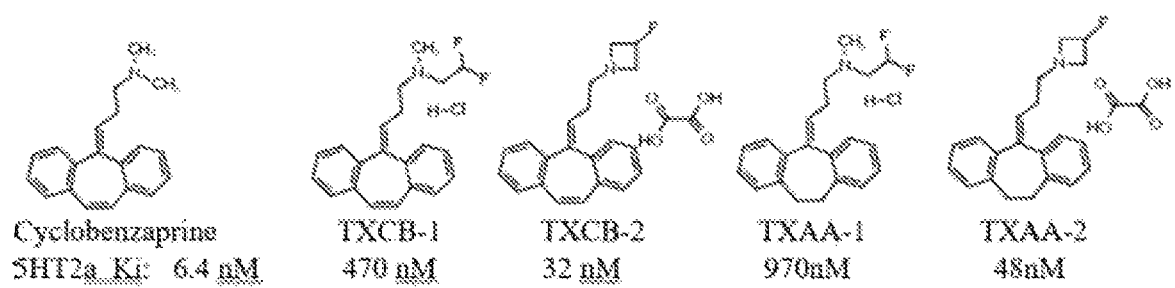
FIG. 2 shows the structures of four analogs of cyclobenzaprine and their anti-5-HT2a activities.

Disclosed herein are cyclobenzaprine analogs that demonstrate inhibition of the 5HT2a receptor (see FIG. 2 for structures and anti-5HT2a activities of some of the analogs disclosed herein and cyclobenzaprine). The beta-fluoro alkyl groups in all 4 molecules and the azetidine rings in TXCB-2 and TXAA-2 are expected to decrease the rates of metabolism alpha to nitrogen, decreasing the rate at which undesirable nor-cyclobenzaprine-like metabolites are formed. Methods of making the cyclobenzaprine analogs are detailed in the Examples.

The present disclosure relates to cyclobenzaprine analogs having the general Formula A shown below

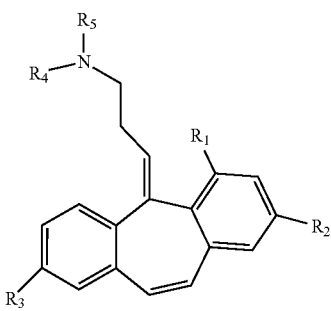

Formula A

In another aspect, the present disclosure relates to amitriptyline analogs having the general formula B shown below

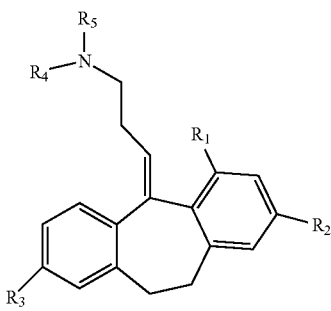

Formula B wherein for both Formula A and Formula B:

$R_1$ is H, $C_{1-4}$-alkyl, $C_{1-4}$-alkoxy; $R_2$ is H, Br, $(CH_2)_nCO_2R$ where n=0 to 3 and R=$C_{1-4}$-alkyl, $C_{1-4}$-alkoxy, halogen; $R_3$ is H, $C_{1-4}$-alkoxy, OH, OCOR where R=$C_{1-4}$-alkyl; $R_4$ is $C_{1-4}$-alkyl wherein if $R_4$ is ethyl the terminus carbon can be optionally substituted by fluorine one to three times; and $R_5$ is $C_{1-4}$-alkyl; $R_4$ and $R_5$ taken together can form a fused 4-membered saturated ring optionally substituted with fluorine.

In one embodiment $R_1$, $R_2$, and $R_3$ are H, $R_4$ is $C_{1-4}$-alkyl and $R_5$ is $C_{1-4}$-alkyl.

In another embodiment $R_1$, $R_2$, and $R_3$ are H, $R_4$ is ethyl that is substituted with fluorine and optionally substituted with methyl, methoxy, $CF_3$, or $CHF_2$ and $R_5$ is $C_{1-4}$-alkyl.

In another embodiment, $R_1$, $R_2$, and $R_3$ are H, $R_4$ is ethyl that is optionally substituted with fluorine and $R_5$ is methyl.

In yet another embodiment, $R_1$, $R_2$, and $R_3$ are H and $R_4$ and $R_5$ taken together form a fused 4-membered ring that is optionally substituted with fluorine.

In an embodiment, $R_1$, $R_2$, and $R_3$ are H, $R_4$ is $C_{1-4}$-alkyl and $R_5$ is $C_{1-4}$-alkyl.

In another embodiment, $R_1$ is $C_{1-4}$-alkyl, $R_2$ is H, $R_3$ is $C_{1-4}$-alkoxy, $R_4$ is $C_{1-4}$-alkyl and $R_5$ is $C_{1-4}$-alkyl.

In another embodiment, $R_1$ is $C_{1-4}$-alkyl, $R_2$ is H, $R_3$ is OCOR where R=$C_{1-4}$-alkyl, $R_4$ is $C_{1-4}$-alkyl and $R_5$ is $C_{1-4}$-alkyl.

In still another embodiment, $R_1$ is $C_{1-4}$-alkyl, $R_2$ is $(CH_2)_nCO_2R$ where n=0 and R=methyl, $R_3$ is H, $R_4$ is $C_{1-4}$-alkyl and $R_5$ is $C_{1-4}$-alkyl.

In another embodiment, $R_1$ is $C_{1-4}$-alkyl, $R_2$ is $C_{1-4}$-alkoxy, $R_3$ is H, $R_4$ is $C_{1-4}$-alkyl and $R_5$ is $C_{1-4}$-alkyl.

In another embodiment, $R_1$ $C_{1-4}$-alkoxy, $R_2$ is H, $R_3$ is H, $R_4$ is $C_{1-4}$-alkyl and $R_5$ is $C_{1-4}$-alkyl.

In an embodiment, $R_1$ is $C_{1-4}$-alkyl, $R_2$ is H, $R_3$ is OH, $R_4$ is $C_{1-4}$-alkyl and $R_5$ is $C_{1-4}$-alkyl.

In another embodiment, $R_1$ is $C_{1-4}$-alkyl, $R_2$ is $(CH_2)_nCO_2R$ where n is 0 and R is $C_{1-4}$-alkyl, $R_3$ is H, $R_4$ is $C_{1-4}$-alkyl and $R_5$ is $C_{1-4}$-alkyl.

In another embodiment, $R_1$ is H, $R_2$ and $R_3$ are $C_{1-4}$-alkoxy,

In an embodiment, $R_1$ is $C_{1-4}$-alkyl, $R_2$ is Br, $R_3$ is H, $R_4$ is $C_{1-4}$-alkyl and $R_5$ is $C_{1-4}$-alkyl.

Another aspect of the present disclosure are deuterated compounds of Formula A and Formula B. A deuterated drug is a small molecule medicinal product in which one or more of the hydrogen atoms contained in the drug molecule have been replaced by it heavier stable isotope deuterium. Deuterium containing drugs may have a longer half-life due to the drugs lower rates of metabolism.

In another aspect, the present disclosure relates to deuterated compounds having the general Formula C shown below

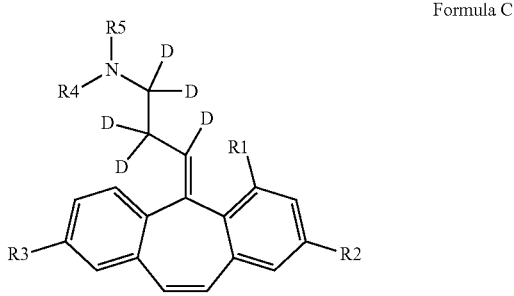

Formula C

Where $R_1$-$R_3$ are the same as Formula A.

$R_4$ and $R_5$ are deuterated as follows:

$R_4$=$R_5$=$CD_3$ $R_4$,$R_5$=$CD_2CDFCD_2$ $R_4$,$R_5$=$CD_2CD_2CD_2$

In another aspect, the present disclosure relates to deuterated compounds having the general Formula D shown below

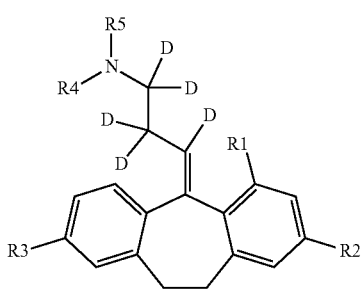

R₁-R₃ are the same as Formula B.
R₄ and R₅ are deuterated as follows:
R₄=R₅=CD₃
R₄,R₅=CD₂CDFCD₂
R₄,R₅=CD₂CD₂CD₂
R₄=CD₃, R₅=CD₂CHF₂

In some aspects disclosed herein is (2,2-Difluoro-ethyl)-[3-(10,11-dihydro-dibenzo[a,d]cyclohepten-5-ylidene)-propyl]-methyl-amine; hydrochloride as shown in Formula I. In some aspects disclosed herein (2,2-Difluoro-ethyl)-[3-(10,11-dihydro-dibenzo[a,d]cyclohepten-5-ylidene)-propyl]-methyl-amine is a free base or a salt of a pharmaceutically acceptable acid other than hydrochloric, preferably without limitation nitric, sulfuric, methanesulfonic, ethylsulfonic, hydroxyethanesulfonic, sulfosalicylic, ethanedisulfonic, methylsulfuric, or trifluoroacetic.

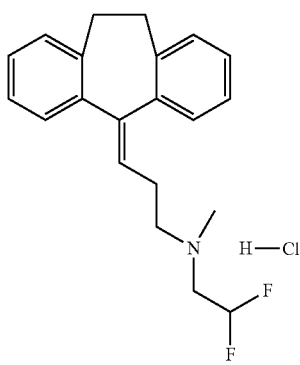

Formula I

In some aspects disclosed herein is a pharmaceutical composition comprising (2,2-Difluoro-ethyl)-[3-(10,11-dihydro-dibenzo[a,d]cyclohepten-5-ylidene)-propyl]-methyl-amine; hydrochloride with a pharmaceutically acceptable carrier, diluent or excipient. In some aspects disclosed herein (2,2-Difluoro-ethyl)-[3-(10,11-dihydro-dibenzo[a,d]cyclohepten-5-ylidene)-propyl]-methyl-amine is pharmaceutical composition comprising a free base or a salt of a pharmaceutically acceptable acid other than hydrochloric, preferably without limitation nitric, sulfuric, methanesulfonic, ethylsulfonic, hydroxyethanesulfonic, sulfosalicylic, ethanedisulfonic, methylsulfuric, or trifluoroacetic; and a pharmaceutically acceptable carrier, diluent or excipient.

In some aspects disclosed herein is (3-Dibenzo[a,d]cyclohepten-5-ylidene-propyl)-(2,2-difluoro-ethyl)-methyl-amine; hydrochloride as shown in Formula II. In some aspects disclosed herein is (3-Dibenzo[a,d]cyclohepten-5-ylidene-propyl)-(2,2-difluoro-ethyl)-methyl-amine as a free base or a salt of a pharmaceutically acceptable acid other than hydrochloric, preferably without limitation nitric, sulfuric, methanesulfonic, ethylsulfonic, hydroxyethanesulfonic, sulfosalicylic, ethanedisulfonic, methylsulfuric, or trifluoroacetic.

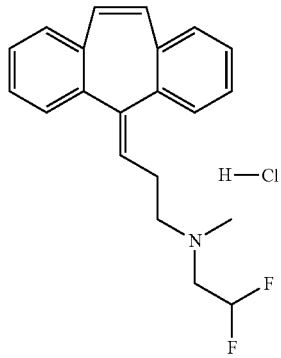

Formula II

In some aspects disclosed herein is a pharmaceutical composition comprising (3-Dibenzo[a,d]cyclohepten-5-ylidene-propyl)-(2,2-difluoro-ethyl)-methyl-amine; hydrochloride with a pharmaceutically acceptable carrier, diluent or excipient. In some aspects disclosed herein (3-Dibenzo[a,d]cyclohepten-5-ylidene-propyl)-(2,2-difluoro-ethyl)-methyl-amine is a pharmaceutical composition comprising a free base or a salt of a pharmaceutically acceptable acid other than hydrochloric, preferably without limitation nitric, sulfuric, methanesulfonic, ethylsulfonic, hydroxyethanesulfonic, sulfosalicylic, ethanedisulfonic, methylsulfuric, or trifluoroacetic; and a pharmaceutically acceptable carrier, diluent or excipient.

In some aspects disclosed herein is 1-[3-(10,11-Dihydro-dibenzo[a,d]cyclohepten-5-ylidene)-propyl]-3-fluoro-azetidine, oxalate salt as shown in Formula III. In some aspects disclosed herein 1-[3-(10,11-Dihydro-dibenzo[a,d]cyclohepten-5-ylidene)-propyl]-3-fluoro-azetidine is a free base or a salt of a pharmaceutically acceptable acid other than oxalic, including without limitation malic, maleic, methanesulfonic, ethylsulfonic, hydroxyethanesulfonic, methylsulfuric, gluconic, or tartaric.

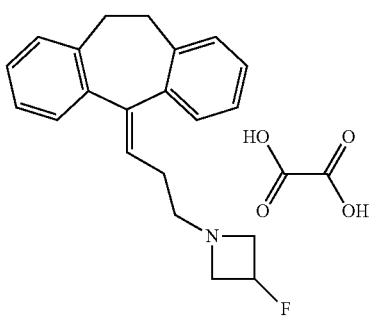

Formula III

In some aspects disclosed herein is a pharmaceutical composition comprising 1-[3-(10,11-Dihydro-dibenzo[a,d]cyclohepten-5-ylidene)-propyl]-3-fluoro-azetidine, oxalate salt with a pharmaceutically acceptable carrier, diluent or excipient. In some aspects disclosed herein 1-[3-(10,11-Dihydro-dibenzo[a,d]cyclohepten-5-ylidene)-propyl]-3-fluoro-azetidine is a pharmaceutical composition comprising a free base or a salt of a pharmaceutically acceptable acid other than oxalic, including without limitation malic, maleic, methanesulfonic, ethylsulfonic, hydroxyethanesulfonic, methylsulfuric, gluconic, or tartaric; and a pharmaceutically acceptable carrier, diluent or excipient.

In some aspects disclosed herein is 1-(3-Dibenzo[a,d]cyclohepten-5-ylidene-propyl)-3-fluoro-azetidine, oxalate salt as shown in Formula IV. In some aspects disclosed herein 1-(3-Dibenzo[a,d]cyclohepten-5-ylidene-propyl)-3-fluoro-azetidine is a free base or a salt of a pharmaceutically acceptable acid other than oxalic, including without limitation malic, maleic, methanesulfonic, ethylsulfonic, hydroxyethanesulfonic, methylsulfuric, gluconic, or tartaric.

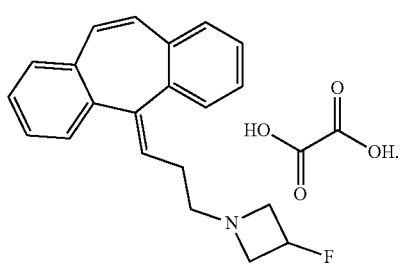

Formula IV

In some aspects disclosed herein is a pharmaceutical composition comprising 1-(3-Dibenzo[a,d]cyclohepten-5-ylidene-propyl)-3-fluoro-azetidine, oxalate salt with a pharmaceutically acceptable carrier, diluent or excipient. In some aspects disclosed herein 1-[3-(10,11-Dihydro-dibenzo[a,d]cyclohepten-5-ylidene)-propyl]-3-fluoro-azetidine is a pharmaceutical composition comprising a free base or a salt of a pharmaceutically acceptable acid other than oxalic, including without limitation malic, maleic, methanesulfonic, ethylsulfonic, hydroxyethanesulfonic, methylsulfuric, gluconic, or tartaric; and a pharmaceutically acceptable carrier, diluent or excipient.

Additional compounds disclosed herein include the following:

TABLE 1

Cyclobenzaprine and Amitriptyline analogs

| Structure | Name |
|---|---|
| (structure with deuterated azetidine and propyl, fluoro substituent, dibenzocycloheptene) | 1-(3-Dibenzo[a,d]cyclohepten-5-ylidene-d5-propyl)-3-fluoro-pentadeutero-azetidine |
| (structure with bis-CD3 on N, deuterated propyl, dibenzocycloheptene) | bis(methyl-D3)-11,12,12,13,13-pentadeutero-cyclobenzaprine |

TABLE 1-continued
Cyclobenzaprine and Amitriptyline analogs
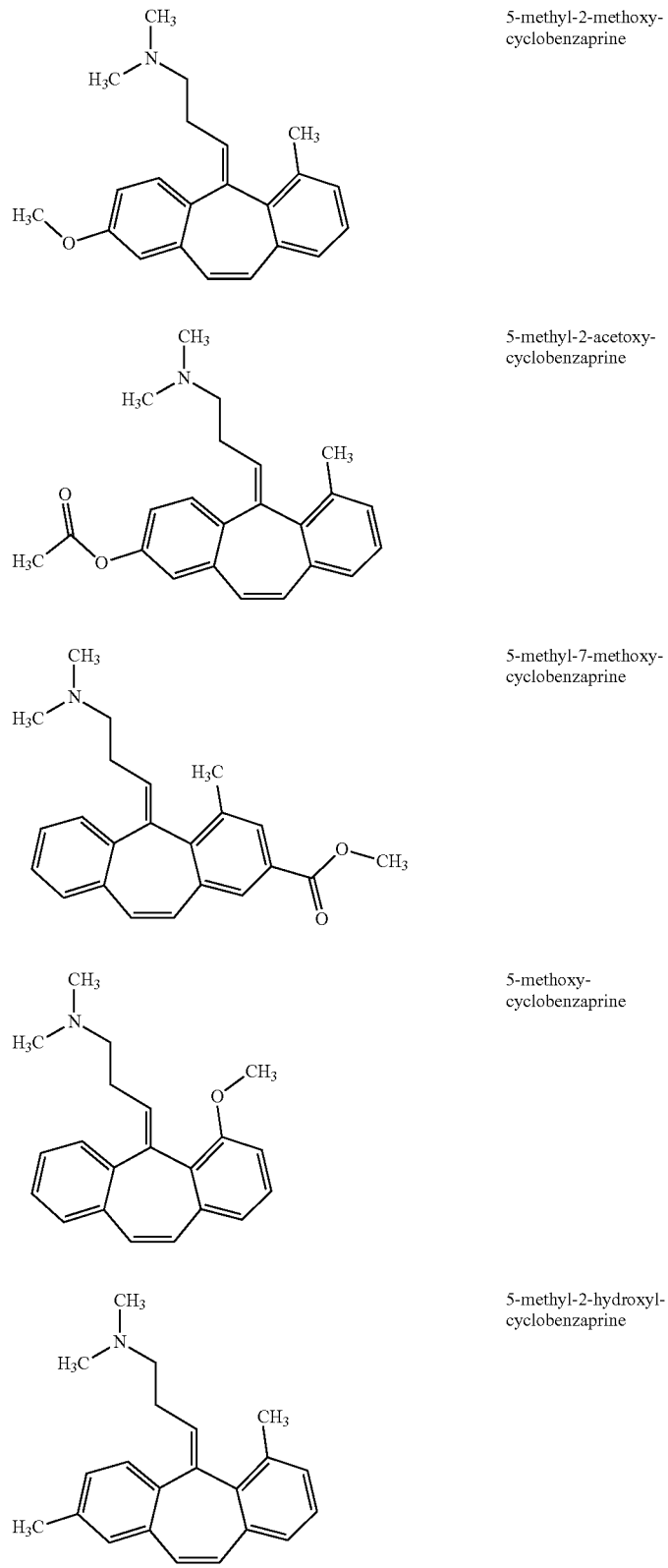
5-methyl-2-methoxy-cyclobenzaprine
5-methyl-2-acetoxy-cyclobenzaprine
5-methyl-7-methoxy-cyclobenzaprine
5-methoxy-cyclobenzaprine
5-methyl-2-hydroxyl-cyclobenzaprine TABLE 1-continued Cyclobenzaprine and Amitriptyline analogs 5-methyl-2-butoxycarbonyl-cyclobenzaprine 2,7-dimethoxy-cyclobenzaprine 1-(3-Dibenzo[a,d]cyclohepten-5-ylidene-propyl)-azetidine In one aspect disclosed herein are methods for treating or preventing post-traumatic stress disorder (PTSD) or one of its symptoms. The method comprises administering to a human in need of such treatment a pharmaceutical composition comprising an analog of cyclobenzaprine and or amitriptyline as defined in the the disclosure and claims that decrease the rates of metabolism alpha to nitrogen, decreasing the rate at which undesirable nor-cyclobenzaprine-like metabolites are formed. In some embodiments of this aspect the analog is (2,2-Difluoro-ethyl)-[3-(10,11-dihydro-dibenzo[a,d]cyclohepten-5-ylidene)-propyl]-methyl-amine; hydrochloride, (3-Dibenzo[a,d]cyclohepten-5-ylidene-propyl)-(2,2-difluoro-ethyl)-methyl-amine; hydrochloride; 1-[3-(10,11-Dihydro-dibenzo[a,d]cyclohepten-5-ylidene)-propyl]-3-fluoro-azetidine, oxalate salt; or 1-(3-Dibenzo[a,d]cyclohepten-5-ylidene-propyl)-3-fluoro-azetidine, oxalate salt as shown in FIG. 2. The symptom may be a sleep disturbance or a non-sleep disturbance.

The term a "sleep disturbance" covers symptoms including difficulty falling asleep, early morning awakening, nightmares, and sleep of poor quality. The quality of sleep ("sleep disturbance") may be determined, inter alia, by asking the patient if he/she awakened tired or nonrefreshed "never," "seldom," "often or usually," or "always." Replies of "often or usually" or "always" may be scored as positive and other replies as negative. Patients' reports of well-being or relief from "zombie" or "spacey" feelings, feelings of being "run down," and having difficulty concentrating during waking hours are indications of better quality of sleep or deep, refreshing sleep. A rating scale commonly used to assess sleep quality is the Functional Outcomes of Sleep Questionnaire (FOSQ) is described in Weaver et al., (1997), An instrument to measure functional status outcomes for disorders of excessive sleepiness. 20(10):835-43.

The term a "non-sleep disturbance" covers symptoms including recurrent and intrusive distressing recollections of the event, including images, thoughts, or perceptions; acting or feeling as if the traumatic event were recurring (includes a sense of reliving the experience, illusions, hallucinations, and dissociative flashback episodes, including those that occur upon awakening or when intoxicated; intense psychological distress at exposure to internal or external cues that symbolize or resemble an aspect of the traumatic event; physiological reactivity on exposure to internal or external cues that symbolize or resemble an aspect of the traumatic event; persistent avoidance of stimuli associated with the trauma and numbing of general responsiveness (not present before the trauma), as indicated by three (or more) of the following: (1) difficulty falling or staying asleep, (2) irritability or outbursts of anger, (3) difficulty concentrating, (4) hypervigilance, or (5) an exaggerated startle response; persistent symptoms of increased arousal (not present before the trauma), as indicated by two (or more) of the following: difficulty falling or staying asleep, irritability or outbursts of anger, difficulty concentrating, hypervigilance, exaggerated startle response. These symptoms are commonly measured using the Clinician Administered PTSD Scale (Blake et al., (1995). The development of a clinician-administered PTSD scale. *Journal of Traumatic Stress,* 8, 75-90).

The analogs of cyclobenzaprine and amitriptyline disclosed herein include metabolites thereof, prodrugs, and analogs for which one or more hydrogen atoms have been replaced by deuterium. Methods for making prodrugs are readily known in the art (e.g., Balant, L. P., Prodrugs for the Improvement of Drug Absorption Via Different Routes of Administration, *Eur. J. Drug Metab. Pharmacokinet.* 15:143-153 (1990); and Bundgaard, H., Novel Chemical Approaches in Prodrug Design, *Drugs of the Future* 16:443-458 (1991); incorporated by reference herein).

As used herein, a "therapeutically effective amount" of cyclobenzaprine analog and or amitriptyline analog for the purposes of this disclosure refers to the amount of the compound that prevents or alleviates or eliminates or interferes with one of the symptoms associated with PTSD. A physician can readily determine when symptoms are prevented or alleviated or eliminated, for example through clinical observation of a subject, or through reporting of symptoms by the subject during the course of treatment. One skilled in the art can readily determine an effective amount of cyclobenzaprine analog to be administered, by taking into account factors such as the size, weight, age and sex of the subject, the extent of disease penetration or persistence and severity of symptoms, and the route of administration. Generally, a therapeutically effective amount of cyclobenzaprine analog administered to a subject is between 0.1 mg to about 50 mg/day, between 0.5 to about 30 mg/day, or between 1 mg and 20 mg/day. Higher or lower doses are also contemplated.

In one embodiment, the cyclobenzaprine analog and or amitriptyline analog is administered at a very low dose to minimize side effects observed at higher doses. The very low doses include doses of less than 5 mg/day or less than 2.5 mg/day. Even lower doses are also contemplated. Generally, cyclobenzaprine analog and or amitriptyline analog therapy can be carried out indefinitely to alleviate the symptoms of interest and frequency of dosage may be changed to be taken as needed. The period of treatment should be carried out for as long as necessary to alleviate one or more of the PTSD symptoms and the cyclobenzaprine analog administered at night-time and at an appropriate dose.

In another embodiment of the invention, the cyclobenzaprine analog and or amitriptyline analog is administered in combination with a drug which may further alleviate the symptoms of PTSD. The drugs may be administered sequentially or concurrently with the cyclobenzaprine analog. The drugs include an alpha-I-adrenergic receptor antagonist, a beta-adrenergic antagonist, an anticonvulsant, a selective serotonin reuptake inhibitor or a serotonin-norepinephrine reuptake inhibitor. Exemplary selective serotonin reuptake inhibitors or serotonin-norepinephrine reuptake inhibitors include, but are not limited to, biproprion (at a dose between about 105 mg and 450 mg/day), citalopram (at a dose between about 10 mg and 40 mg/day), desvenlafaxine (at a dose between about 50 mg and 400 mg/day), duloxetine (at a dose between about 40 mg and 120 mg/day), escitalopram (at a dose between about 10 mg and 20 mg/day), fluoxetine (at a dose between about 20 mg and 80 mg/day), fluvoxamine (at a dose between about 100 mg and 300 mg/day), milnacipran (at a dose between about 30 mg and 200 mg/day), paroxetine (at a dose between about 20 mg and 50 mg/day), sertraline (at a dose between about 50 mg and 200 mg/day), tradodone (at a dose between about 150 mg and 600 mg/day), and venlafaxine (at a dose between about 75 mg and 225 mg/day), Exemplary anticonvulsants include, but are not limited to carbamazepine (at a dose between about 400 mg and 1200 mg/day), gabapentin (at a dose between about 900-1800 mg/day), lamotrigine (at a dose between about 100 mg and 400 mg/day), oxcarbazepine (at a dose between about 1200 mg and 2400 mg/day), pregabalin (at a dose between about 150 mg and 600 mg/day), tiagabine (at a dose between about 32 mg and 56 mg/day), topiramate (at a dose between about 200 mg and 400 mg/day), and valproate (at a dose between about 1200 mg and 1500 mg). Exemplary alpha-1-adrenergic receptor antagonists include, but are not limited to, prazosin administered at a dose of between about 0.5 mg to 15 mg/day.

In another aspect, the invention may be employed for treating or preventing the development (either the initiation, consolidation or perpetuation) of a PTSD symptom following a traumatic event. A traumatic event is defined as a direct personal experience that involves actual or threatened death or serious injury, or other threat to one's physical integrity; or witnessing an event that involves death, injury, or a threat to the physical integrity of another person; or learning about unexpected or violent death, serious harm, or threat of death or injury experienced by a family member or other close associate. Traumatic events that are experienced directly include, but are not limited to, military combat, violent personal assault (sexual assault, physical attack, robbery, mugging), being kidnapped, being taken hostage, terrorist attack, torture, incarceration as a prisoner of war or in a concentration camp, natural or manmade disasters, severe automobile accidents, or being diagnosed with a life-threatening illness. For children, sexually traumatic events may include developmentally inappropriate sexual experiences without threatened or actual violence or injury. Witnessed events include, but are not limited to, observing the serious injury or unnatural death of another person due to violent assault, accident, war, or disaster or unexpectedly witnessing a dead body or body parts. Events experienced by others that are learned about include, but are not limited to, violent personal assault, serious accident, or serious injury experienced by a family member or a close friend; learning about the sudden, unexpected death of a family member or a close friend; or learning that one's child has a life-threatening disease. The disorder may be especially severe or long lasting when the stressor is of human design (e.g., torture, rape).

The initiation of a PTSD symptom occurs immediately following the traumatic event during which the symptoms of PTSD appear and become increasingly severe. It is thought that there is a kind of "learning" or reinforcement process in which the memories of the trauma are engrained in the mind. As these memories become more fixed, symptoms such as flashbacks and nightmares grow in severity and frequency. It is though that interventions during this critical time may prevent some patients from developing fully blown PTSD. The consolidation of a PTSD symptom typically occurs during the weeks and months following a traumatic event. A person's memories of that event become consolidated into highly vivid and concrete memories that are re-experienced with increasing frequency either as flashbacks or nightmares. During this time hyperarousal symptoms and avoidant behavior become increasingly severe and disabling. The perpetuation of a PTSD symptom occurs once traumatic memories are consolidated, and the reexperiencing symptoms (flashbacks and nightmares) and the hyperarousal symptoms become persistent and remain at a level that is functionally disabling to the patient.

By the method of the invention, the different phases of PTSD development may be treated with a pharmaceutical composition comprising a cyclobenzaprine analog at different time intervals after the traumatic event. For example, to treat the initiation phase of PTSD, the cyclobenzaprine analog and or amitriptyline analog needs to be administered to a subject in need soon after the traumatic event, for example within the first week, within the second week, within the third week or within the fourth week or longer. Whereas to treat the consolidation phase of PTSD, the cyclobenzaprine analog has to be administered later after the traumatic event and later during the development of the symptoms, for example within the first month, within the second month or within the third month or longer. Typically to treat the perpetuation phase of PTSD the cyclobenzaprine analog is administered 3 months or longer after the traumatic event, for example within the third month, within the fourth month, within the fifth month or longer. As a result of cyclobenzaprine analog treatment at the initiation, consolidation, or perpetuation phase, PTSD symptoms will be ameliorated or be eliminated.

The method comprises administering to a human in need of such treatment a pharmaceutical composition comprising a cyclobenzaprine analog disclosed herein in a therapeutically effective amount and a therapeutically acceptable carrier. The therapeutically effective amount of cyclobenzaprine analog administered to a subject is between 0.1 mg to about 50 mg/day, between 0.5 to about 30 mg/day, or between 1 mg and 20 mg/day. Higher or lower doses are also contemplated. In one particular embodiment, the cyclobenzaprine analog is administered at a very low dose to minimize side effects observed at higher doses. The very low doses include doses of less than 10 mg/day or less than 5 mg/day or less than 2.5 mg/day. Even lower amounts are also contemplated. In another embodiment of the invention, cyclobenzaprine analog and or amitriptyline analog is administered in combination with a drug which may further alleviate the symptoms of PTSD. The drugs may be administered sequentially or concurrently with the cyclobenzaprine. The drugs include an alpha-1-adrenergic receptor antagonist, a beta-adrenergic antagonist, an anticonvulsant, a selective serotonin reuptake inhibitor or a serotonin-norepinephrine reuptake inhibitor. Exemplary selective serotonin reuptake inhibitors or serotonin-norepinephrine reuptake inhibitors include, but are not limited to, buproprion (at a dose between about 105 mg and 450 mg/day), citalopram (at a dose between about 10 mg and 40 mg/day), desvenlafaxine (at a dose between about 50 mg and 400 mg/day), duloxetine (at a dose between about 40 mg and 120 mg/day), escitalopram (at a dose between about 10 mg and 20 mg/day), fluoxetine (at a dose between about 20 mg and 80 mg/day), fluvoxamine (at a dose between about 100 mg and 300 mg/day), milnacipran (at a dose between about 30 mg and 200 mg/day), paroxetine (at a dose between about 20 mg and 50 mg/day), sertraline (at a dose between about 50 mg and 200 mg/day), tradodone (at a dose between about 150 mg and 600 mg/day), and venlafaxine (at a dose between about 75 mg and 225 mg/day), Exemplary anticonvulsants include, but are not limited to carbamazepine (at a dose between about 400 mg and 1200 mg/day), gabapentin (at a dose between about 900-1800 mg/day), lamotrigine (at a dose between about 100 mg and 400 mg/day), oxcarbazepine (at a dose between about 1200 mg and 2400 mg/day), pregabalin (at a dose between about 150 mg and 600 mg/day), tiagabine (at a dose between about 32 mg and 56 mg/day), topiramate (at a dose between about 200 mg and 400 mg/day), and valproate (at a dose between about 1200 mg and 1500 mg). Exemplary alpha-1-adrenergic receptor antagonists include, but are not limited to, prazosin administered at a dose of between about 0.5 mg to 15 mg/day.

In a further aspect, the invention is a pharmaceutical composition. The pharmaceutical composition comprises a therapeutically effective amount of cyclobenzaprine analog and or amitriptyline analog in combination with a drug selected from the group consisting of an alpha-1-adrenergic receptor antagonist, a beta-adrenergic antagonist, and an anticonvulsant. Generally, the amount of cyclobenzaprine analog in the pharmaceutical composition is between 0.1 mg to about 50 mg, between 0.5 to about 30 mg, or between 1 mg and 20 mg. Higher or lower doses are also contemplated. In one particular embodiment the amount of cyclobenzaprine analog and or amitriptyline analog is very low to minimize side effects observed with higher amounts. The very low amounts are of less than 10 mg or less than 5 mg or less than 2.5 mg. Even lower amounts are also contemplated. In another embodiment of the invention, cyclobenzaprine analog is combined with a drug which may further alleviate the symptoms of PTSD. The drugs include an alpha-I-adrenergic receptor antagonist, a beta-adrenergic antagonist, an anticonvulsant, a selective serotonin reuptake inhibitor or a serotonin-norepinephrine reuptake inhibitor. Exemplary anticonvulsants include, but are not limited to carbamazepine (400 mg to 1200 mg), gabapentin (900 mg to 1800 mg), lamotrigine (100 mg to 400 mg), oxcarbazepine (1200 mg to 2400 mg), pregabalin (150 mg to 600 mg), tiagabine (32 mg to 56 mg), topiramate (200 mg to 400 mg), and valproate (1200 mg to 1500 mg). An exemplary alpha-1-adrenergic receptor antagonists includes, but is not limited to, prazosin in the amount of 0.5 mg to 15 mg. An exemplary selective serotonin reuptake inhibitor is escitalopram (in the amount of 10 mg and 20 mg).

Any suitable route of administration may be employed for providing the patient with an effective dosage of cyclobenzaprine analog and or amitriptyline analog. For example, buccal, oral, rectal, parenteral, transdermal, subcutaneous, sublingual, intranasal, intramuscular, intrathecal and the like may be employed as appropriate. The term parenteral as used herein includes subcutaneous, intracutaneous, intravenous, intramuscular, intra-articular, intrasynovial, intrasternal, intrathecal, intralesional and intracranial injection or infusion techniques. Dosage forms include tablets, such as scored tablets, coated tablets, or orally dissolving tablets; thin films, caplets, capsules (e.g. hard gelatin capsules), troches, dragees, dispersions, suspensions, solutions, patches and the like, including sustained release formulations well known in the art. In one preferred embodiment, the dosage form is an orally dissolving tablet or a thin film.

By "pharmaceutically acceptable carrier" is meant any diluent or excipient that is compatible with the other ingredients of the formulation, and which is not deleterious to the recipient. The pharmaceutically acceptable carrier can be selected on the basis of the desired route of administration, in accordance with standard pharmaceutical practices. Pharmaceutical compositions of the invention for parenteral administration can take the form of an aqueous or nonaqueous solution, dispersion, suspension or emulsion. In preparing pharmaceutical compositions of the invention for parenteral administration, cyclobenzaprine analog and or amitriptyline analog can be mixed with a suitable pharmaceutically acceptable carrier such as water, oil (particularly a vegetable oil), ethanol, saline solutions (e.g., normal saline), aqueous dextrose (glucose) and related sugar solutions, glycerol, or glycols such as propylene glycol or polyethylene glycol. Pharmaceutical compositions of the invention for parenteral administration preferably contain a water-soluble salt of a cyclobenzaprine analog. Stabilizing agents, antioxidizing agents and preservatives can also be added to the pharmaceutical compositions for parenteral administration. Suitable antioxidizing agents include sulfite, ascorbic acid, citric acid and its salts, and sodium EDTA. Suitable preservatives include benzalkonium chloride, methyl- or propyl-paraben, and chlorbutanol.

In preparing pharmaceutical compositions of the invention for oral administration, a cyclobenzaprine analog can be combined with one or more solid or liquid inactive ingredients to form tablets, capsules, pills, powders, granules or other suitable oral dosage forms. For example, cyclobenzaprine analog and or amitriptyline analog can be combined with at least one pharmaceutically acceptable carrier such as a solvent, filler, binder, humectant, disintegrating agent, solution retarder, absorption accelerator, wetting agent absorbent or lubricating agent. In one embodiment, a cyclobenzaprine analog is combined with carboxymethylcellulose calcium, magnesium stearate, mannitol or starch, and is formed into tablets by conventional tableting methods.

Pharmaceutical compositions of the invention can be formulated so as to provide buccal absorption including thin film formulations and orally dissolving tablets to provide faster absorption than the oral/GI route and to bypass first-pass hepatic metabolism of cyclobenzaprine by cytochrome P-450 3A4 as a CYP3A substrate. Preferably, a controlled-release pharmaceutical composition of the invention is capable of releasing a cyclobenzaprine analog into a subject at a rapid onset, so as to maintain a substantially constant or desired pharmacological activity for a given period of time, reduce or remove the effect of food on absorption, and to provide elimination of the drug and metabolites from the body with a reduced terminal elimination phase.

Pharmaceutical compositions of the invention can also be formulated so as to provide controlled-release of a cyclobenzaprine analog and or amitriptyline analog upon administration of the composition to a subject. Preferably, a controlled-release pharmaceutical composition of the invention is capable of releasing a cyclobenzaprine analog into a subject at a desired rate, so as to maintain a substantially constant or desired pharmacological activity for a given period of time. As used herein, a "controlled-release component" is a compound such as a lipid or mixture of lipids, liposome and/or microsphere that induces the controlled-release of a cyclobenzaprine analog into the subject upon exposure to a certain physiological compound or condition. For example, the controlled-release component can be biodegradable, activated by exposure to a certain pH or temperature, by exposure to an aqueous environment, or by exposure to enzymes.

Formulation of controlled-release pharmaceutical compositions of the invention is within the skill in the art. Controlled release formulations suitable for use in the present invention are described in, for example, U.S. Pat. No. 5,674,533 (liquid dosage forms), U.S. Pat. No. 5,591,767 (liquid reservoir transdermal patch), U.S. Pat. No. 5,120,548 (device comprising swellable polymers), U.S. Pat. No. 5,073,543 (ganglioside-liposome vehicle), U.S. Pat. No. 5,639,476 (stable solid formulation coated with a hydrophobic acrylic polymer), and enteric-coated capsules for rapid release in the duodenum, the entire disclosures of which are herein incorporated by reference. The enteric-coated capsules may contain either the cyclobenzaprine analog free base or a free base precursor such as a cyclobenzaprine analog salt/mannitol eutectic combined with dipotassium phosphate. The free base form of the cyclobenzaprine analog should more rapidly permeate the duodenal lumen than salt forms, enabling a higher maximum plasma concentration than any salt form.

Biodegradable microparticles can also be used to formulate controlled-release pharmaceutical compositions suitable for use in the present invention, for example as described in U.S. Pat. Nos. 5,354,566 and 5,733,566, the entire disclosures of which are herein incorporated by reference.

In one embodiment, controlled-release pharmaceutical compositions of the invention comprise a cyclobenzaprine analog and a controlled-release component. As used herein, a "controlled-release component" is a compound such as a polymer, polymer matrix, gel, permeable membrane, liposome and/or microsphere that induces the controlled-release of cyclobenzaprine into the subject upon exposure to a certain physiological compound or condition. For example, the controlled-release component can be biodegradable, activated by exposure to a certain pH or temperature, by exposure to an aqueous environment, or by exposure to enzymes. An example of a controlled-release component which is activated by exposure to a certain temperature is a sol-gel. In this embodiment, a cyclobenzaprine analog is incorporated into a sol-gel matrix that is a solid at room temperature. This sol-gel matrix is implanted into a subject having a body temperature high enough to induce gel formation of the sol-gel matrix, thereby releasing the active ingredient into the subject.

In one embodiment, pharmaceutical compositions of the invention may comprise a cyclobenzaprine analog and components that form micelles. Micelles containing a cyclobenzaprine analog in the stomach and proximal small intestine facilitate absorption. Example of a micelle-component which is activated by exposure to a certain temperature is found in U.S. Pat. Nos. 6,761,903; 6,720,001; 6,383,471; 6,309,663; 6,267,985; and 6,248,363, incorporated herein by reference. In this embodiment, a cyclobenzaprine analog is incorporated into a soft-gel capsule. Such components may mimic the augmentation of absorption termed the "food effect", and such formulations may provide more predictable absorption by eliminating the "food effect" from dietary sources.

The composition of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The magnitude of a prophylactic or therapeutic dose of the active ingredient (i.e., cyclobenzaprine analog or metabolite thereof) in the prevention or treatment of a human will vary with the type of affliction, the severity of the patient's affliction and the route of administration. The dose and dose frequency will also vary according to the age, weight and response of the individual patient. However, the dosage will not equal or exceed 5 mgs per day. In a preferred embodiment, one dose is given at bed time or up to several hours before bedtime to facilitate the achievement of deep, refreshing sleep. Bedtime may be any hour of the day at which a person engages in the most extensive period of sleep.

Any of the methods of treatment described above may be combined with psychotherapeutic intervention to improve the outcome of the treatment. Of particular interest is psychotherapeutic intervention directed at either modifying traumatic memories reducing emotional responses to traumatic memories, and including: psychological debriefing, cognitive behavior therapy and eye movement desensitization and reprocessing, systematic desensitization, relaxation training, biofeedback, cognitive processing therapy, stress inoculation training, assertiveness training, exposure therapy, combined stress inoculation training and exposure therapy, combined exposure therapy and relaxation training and cognitive therapy. In each case, the goal of the intervention involves either modifying traumatic memories or reducing emotional responses to traumatic memories. The intended result is generally improvement as evidenced in terms of reducing intrusive combat memories, physiological responding, anxiety, depression and feelings of alienation.

A pharmacogenomic test to measure cytochrome CYP3A4, CYP1A2, CYP3A and CYP2G6 may be used to predict the metabolism of a cyclobenzaprine analog by certain patients in personalized medicine. Thus, the invention is a method for selecting an effective dose of a cyclobenzaprine analog to be administered to a human in need of such treatment to correct for variations in cyclobenzaprine metabolism. The method comprises obtaining a genetic sample from said human and identifying the CYP1A2, CYP3A4, CYP3A or CYP2G6 genotype of said human, for example by using a gene chip or a PCR technique, to identify the alleles of one or more of the genes. Different alleles metabolize cyclobenzaprine at different speeds. For individuals having a cytochrome allele identified to metabolize a cyclobenzaprine analog quickly a higher dose of amitriptyline analog is administered. For individuals having an allele identified to metabolize a cyclobenzaprine analog slowly a lower dose of cyclobenzaprine analog is administered. The genetic test can be sold as a kit with the product to physicians/lab testing services.

The disclosure will now be described with reference to the following examples which illustrate some particular aspects and embodiments of the present application. However, it is to be understood that the particularity of the following description is not to supersede the generality of the preceding detailed description/summary of the aspects and embodiments of the disclosure.

EXAMPLES

The purification of trialkylamine final products in examples 1-4 and 7-18. As free bases, the trialkylamine final products may optionally be purified as follows: 1) Using silica gel chromatography hexane-ethyl acetate, hexane-diethyl ether, dichloromethane-ethyl acetate, dichloromethane-methanol. A volatile trialkylamine such as triethylamine, trimethylamine, or DIPEA at 1-3% of volume may optionally be added to the solvent to improve separation. 2) Using reverse phase chromatography on C18 silica or phenylsilica. As salts, including but not limited to oxalate, chloride, or benzoate, the trialkylamine final products can be purified by recrystallized from a suitable solvent or solvent mixture, including but not limited to isopropanol, methanol, ethanol and their mixtures with ethyl acetate, chloroform, and/or toluene.

Example 1-Preparation of TXAA-1, (2,2-Difluoro-ethyl)-[3-(10,11-dihydro-dibenzo[a,d]cyclohepten-5-ylidene)-propyl]-methyl-amine; hydrochloride

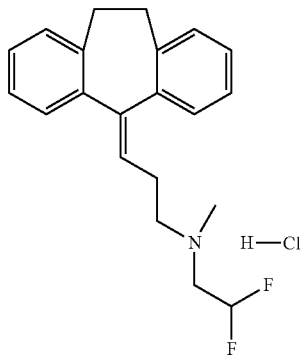

Nortriptyline HCl (1.80 g, 6.00 mmol) was suspended in anhydrous THF (20 mL), DIEA (2.30 mL, 13.2 mmol) was added at room temperature (RT) to give a suspension. The reaction mixture was briefly heated to gentle reflux after which the suspension remained. The suspension was cooled to 5° C., Trifluoro-methanesulfonic acid 2,2-difluoro-ethyl ester (1.414 mL, 6.60 mmol) was added dropwise at 5° C., then the reaction mixture was allowed to slowly warm to RT, and stirred at RT for 14 h after which there was an amber solution with a small amount of suspension. The solvent was evaporated in vacuo to give a solid which was extracted with diethyl ether ($Et_2O$) (200 mL), washed with water (40 mL), brine (40 mL), dried with $MgSO_4$, solvent was evaporated in vacuo to give an oil which was dissolved in dichloromethane (DCM) (6 mL) and purified by $SiO_2$ chromatography using Hex-EtOAc (ethyl acetate) to give an amber oil (1.05 g, 3.2 mmol). This oil was dissolved in $Et_2O$ (3.0 mL), cooled to 5° C., 1 M HCl in $Et_2O$ (6.4 mL, 6.4 mmol) was added dropwise while stirring to give a gum. The solvent was evaporated in vacuo to give a gum which was further evaporated in vacuo (0.5 mm Hg) to give the title compound (1.150 g, 53%) as a hygroscopic foam. LCMS: mass expected for $C_{21}H_{23}F_2N$: 327.18. Found: 328.2 (M+H). $^1H$ NMR (dmso-d6): 6.60 (1H, t, J=54 Hz), 5.78 (1H, t, J=7 Hz), TLC: DCM-MeOH-$HNEt_2$, 90:10:3, SM, Rf 0.35, product, Rf 0.80.

TLC: Hex-EtOAc, 80:20, SM. Rf 0.0, product, Rf 0.38.

Example 2-Preparation of TXCB-1, (3-Dibenzo[a,d]cyclohepten-5-ylidene-propyl)-(2,2-difluoro-ethyl)-methyl-amine; hydrochloride

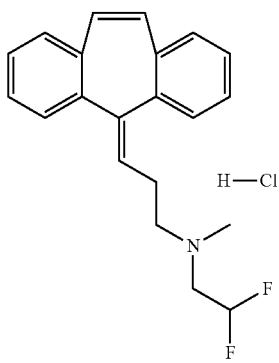

Norcyclobenzaprine (1.57 g, 6.00 mmol), was suspended in anhydrous tetrahydrofuran (THF) (20 mL), N,N-diisopropylethylamine (DIEA) (1.25 mL, 7.20 mmol) was added at RT to give a suspension. The reaction mixture was briefly heated to gentle reflux to give a turbid solution which was cooled to 5° C., Trifluoro-methanesulfonic acid 2,2-difluoro-ethyl ester (1.414 mL, 6.60 mmol) was added dropwise at 5° C., then the reaction mixture was allowed to slowly warm to RT, and stirred at RT for 15 h after which there was a suspension. The solvent was evaporated in vacuo to give an oil which was extracted with Et$_2$O (120 mL), washed with water (20 mL), brine (20 mL), dried with MgSO$_4$. The solvent was evaporated in vacuo to give an oil which was dissolved in DCM (6 mL) and purified by SiO$_2$ chromatography using Hex-EtOAc to give an amber oil (1.70 g, 5.21 mmol). This oil was dissolved in Et$_2$O (5.0 mL), cooled to 5° C., 1 M HCl in Et$_2$O (12 mL, 12 mmol) was added dropwise while stirring to give a gum. The solvent was evaporated in vacuo to give a gum which was further evaporated in vacuo (0.5 mm Hg) to give the title compound (1.514 g, 70%) as a hygroscopic foam. LCMS: mass expected for C$_{21}$H$_{23}$F$_2$N: 325.16. Found: 326.2 (M+H). $^1$H NMR (dmso-d6): 6.5 (1H, br), 5.47 (1H, t, 7 Hz), TLC: DCM-MeOH-HNEt$_2$, 95:5:3, SM, Rf 0.30, product, Rf 0.85.

TLC: Hex-EtOAc, 80:20, SM. Rf 0.0, product, Rf 0.40.

Alternately, the desired molecule is made by combining a 3-fold excess of N-(2,2-difluoroethyl)-methanamine (Yoshida et al., *Bioorganic and Medicinal Chemistry*, 2006, vol. 14 pp 8506-8518) with 3-bromopropylidene)-dibenzosuberene (Novo Nordisk A/S—U.S. Pat. No. 5,595,989) for 72 hours at 25° C. as described in Yoshida et al.

Example 3-Preparation of TXAA-2. 1-[3-(10,11-Dihydro-dibenzo[a,d]cyclohepten-5-ylidene)-propyl]-3-fluoro-azetidine, oxalate salt

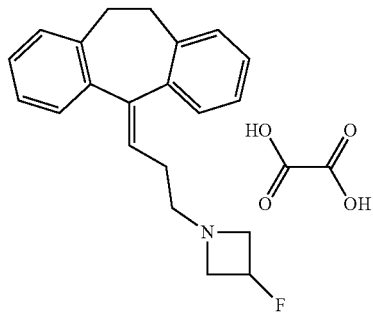

3-Fluoro-azetidine; hydrochloride (0.974 g, 8.73 mmol), cesium carbonate (6.64 g, 20.4 mmol), and 5-(3-bromopropylidene)-10,11-dihydro-5H-dibenzo[a,d]cycloheptene (1.823 g, 5.82 mmol), synthesis in Nordisk A/S—U.S. Pat. No. 5,595,989, were suspended in anhydrous acetonitrile (17.6 mL) using a heavy-walled glass reaction vessel which was sealed and stirred at 75° C. for 16 h to give a white suspension. The reaction mixture was cooled to RT, the solids were filtered off, washed thrice with acetonitrile, the filtrate was concentrated to give an oil which was partitioned between Et$_2$O (120 mL) and water (60 mL). The organic layer was washed with brine (60 mL), dried with MgSO$_4$, the solvent was concentrated to give an oil which was further evaporated in vacuo (0.1 mm Hg) for 14 h at RT to remove 3-fluoro-azetidine to give an oil (1.88 g, approx 4.1 mmol, purity approx 70% by LCMS). The oil was dissolved in Et$_2$O (41 mL), 0.156 M oxalic acid (26.3 mL, 4.11 mmol) in Et$_2$O was added dropwise to the stirred mixture at RT over 40 min using a syringe pump to give a white suspension. The solid was filtered, washed with Et$_2$O thrice to give the oxalate salt as a fluffy white solid (1.63 g, 4.10 mmol, 90% purity by LCMS). This solid was partitioned between 1N NaOH (41 mL) and Et$_2$O (100 mL), the organic layer was washed with water (50 mL), brine (50 mL), dried with MgSO$_4$, the solvent was concentrated to give the free base as an oil. This oil was dissolved in Et$_2$O (41 mL) and treated with 0.156 M oxalic acid (26.3 mL, 4.11 mmol) in Et$_2$O in the same way as described to give the titled compound as a white fluffy solid (1.38 g, 60%). LCMS: mass calc for C$_{21}$H$_{22}$FN: 307.17, found: 308.3 (M+H). $^1$H NMR (DMSO-d$_6$):

Example 4—Preparation of TXCB-2. 1-(3-Dibenzo[a,d]cyclohepten-5-ylidene-propyl)-3-fluoro-azetidine, oxalate salt

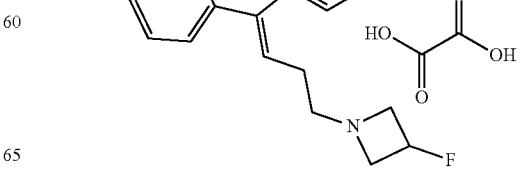

3-Fluoro-azetidine; hydrochloride (977 g, 8.76 mmol), cesium carbonate (6.66 g, 20.45 mmol), and 5-(3-bromopropylidene)-10,11-dihydro-5H-dibenzo[a,d]cycloheptene (1.818 g, 5.84 mmol, synthesis in Nordisk A/S—U.S. Pat. No. 5,595,989) were suspended in anhydrous acetonitrile (17.6 mL) using a heavy-walled glass reaction vessel which was sealed and stirred at 75° C. for 16 h to give a white suspension. The reaction mixture was cooled to RT, the solids were filtered, washed thrice with acetonitrile, the filtrate was concentrated to give an oil which was partitioned between Et$_2$O (120 mL) and water (60 mL). The organic layer was washed with brine (60 mL), dried with MgSO$_4$, the solvent was concentrated to give an oil which was further evaporated in vacuo (0.1 mm Hg) for 14 h at RT to remove 3-fluoro-azetidine to give an oil (1.643 g, approximately 3.39 mmol, purity approximately 63% by LCMS). The oil was dissolved in Et$_2$O (41 mL), 0.156 M oxalic acid (26.3 mL, 4.11 mmol) in Et$_2$O was added dropwise to the stirred mixture at RT over 40 min using a syringe pump to give a white suspension. The solid was filtered, washed with Et$_2$O thrice to give the oxalate salt as a white solid (1.60 g, 4.04 mmol, 90% purity by LCMS). This solid was partitioned between 1 N NaOH (41 mL) and Et$_2$O (100 mL), the organic layer was washed with water (50 mL), brine (50 mL), dried with MgSO$_4$, the solvent was concentrated to give the free base as an oil (1.151 g, 3.77 mmol). This oil was dissolved in Et$_2$O (38 mL) and treated with 0.156 M oxalic acid (24.2 mL, 3.77 mmol) in Et$_2$O in the same way as described to give the titled compound as a white solid (1.25 g, 54%). LCMS: mass calc for C$_{21}$H$_{20}$FN 305.16, found, 306.2 (M+H). $^1$H NMR (DMSO-d$_6$): $^{13}$C NMR (DMSO-d$_6$):

Example 5—Preparation of 5-(3-bromo-d5-propylidene)-5H-dibenzo[a,d]cycloheptene

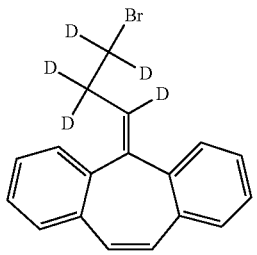 [SMILES: [2H]C(=C1c2ccccc2C=Cc2ccccc21)C([2H])([2H])C([2H])([2H])Br]

A solution of D5-cyclopropylmagnesium bromide in dry THF (prepared from D5 cyclopropylbromide (8.0 g, 0.067 mol), magnesium turnings (1.3 g, 0.053 mol) and dry THF (35 ml)) is placed under an atmosphere of nitrogen. A solution of Dibenzosuberenon (6.0 g, 0.028 mol) in dry THF (15 ml) is added dropwise and when addition is complete the mixture is heated at reflux for 30 minutes. The reaction mixture is cooled on an ice-bath and saturated ammonium chloride (35 ml) is carefully added. The mixture is diluted with water (50 ml) and extracted with diethyl ether (2×50 ml). The combined organic extracts are washed with water, dried (Na$_2$SO$_4$) and the solvent is evaporated in vacuo to give crude 5-hydroxy-5-(d5-cyclopropyl)-dibenzosuberene.

This alcohol (10 mmoles) is combined with CBr$_4$ (20 mmoles), triphenylphosphine (Ph$_3$P) (20 mmoles), N,N-Diisopropylethylamine (DIPEA) (20 mmoles) and tributylphosphine (1 mmoles) in toluene (20 mL) and heated at 100° C. for 1 hour. The reaction is stripped of solvent and the product purified by silica chromatography in hexane-ethyl acetate. (Adapted from N. Sakai, T. Maruyama, T. Konakahara, Synlett, 2009, 2105-2106).

Alternately, this conversion can be carried out by 1. replacing the OH of the 5-hydroxy-5-(d5-cyclopropyl)-dibenzosuberene with OD by repeatedly dissolving in CD$_3$OD and stripping the solvent; and 2. Treating with trimethylsilylbromide as in Anderson et al, U.S. Pat. No. 5,595,989 (1995).

Bromocyclopropane-d5 is commercially available from Toronto Research Chemicals #B682763

Dibenzosuberenone is commercially available from Sigma Aldrich.

Example 6—Preparation of 3-fluoro-pentadeutero-azetidine, deuterochloride salt

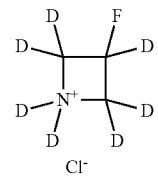

Epichlorohydrin-d5 and diphenylmethylamine are converted to, N-diphenylmethyl-3-hydroxy-d5-azetidine deuterochloride, using the procedure in Bartnik and Marchand, Synlett 1997 pp 1029-1039. After neutralization, the N-diphenylmethyl-3-hydroxy-d5-azetidine is treated with bis(2-methoxyethyl)aminosulfur trifluoride (deoxyfluor), according to Singh and Shreeve, J. Fluorine Chemistry V116 pp 23-26 (2002) to form N-diphenylmethyl-3-fluoro-d5-azetidine. This is deprotected with deuterium in deuterium chloride using Pd/C, following the procedure of Bartnik and Marchand, Synlett 1997 pp 1029-1039 to form 3-fluoro-pentadeutero-azetidine, deuterochloride salt.

Epichlorohydrin-d5 is available from Santa Cruz Biotechnology.

Example 7-Preparation of TXCB-2-D11. 1-(3-Dibenzo[a,d]cyclohepten-5-ylidene-d5-propyl)-3-fluoro-pentadeutero-azetidine, deuterooxalate salt

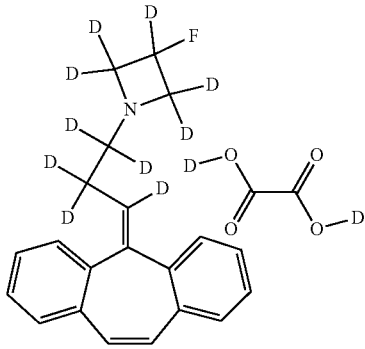

5-(3-bromo-d5-propylidene)-5H-dibenzo[a,d]cycloheptene (from EXAMPLE 5) and 3-fluoro-pentadeutero-azetidine, deuterochloride salt (from EXAMPLE 6) are combined using the procedure in EXAMPLE 4 to make 1-(3-

Dibenzo[a,d]cyclohepten-5-ylidene-d5-propyl)-3-fluoro-pentadeutero-azetidine. This free base is combined with deuterooxalic acid to make the title compound.

Example 8-Preparation of bis(methyl-D3)-11,12,12,13,13-pentadeutero-cyclobenzaprine

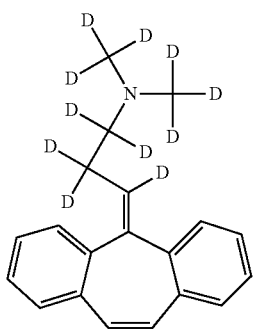 [SMILES: [2H]C(=C1c2ccccc2C=Cc2ccccc21)C([2H])([2H])C([2H])([2H])N(C([2H])([2H])[2H])C([2H])([2H])[2H]]

5-(3-bromo-d5-propylidene)-5H-dibenzo[a,d]cycloheptene (from EXAMPLE 5 and dimethylamine-d7 deuterochloride are combined to make D-11 cyclobenzaprine using the procedure in example 4. This free base is combined with deuterooxalic acid to make the title compound.

Dimethylamine-D7 deuterochloride (MDL number MFCD04118250) dimethylamine-d7 is commercially available from Toronto Research Chemicals. Sigma Aldrich.

Example 9—Preparation of 5-methyl-2-methoxy-cyclobenzaprine

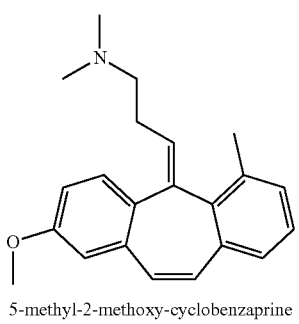

5-methyl-2-methoxy-cyclobenzaprine

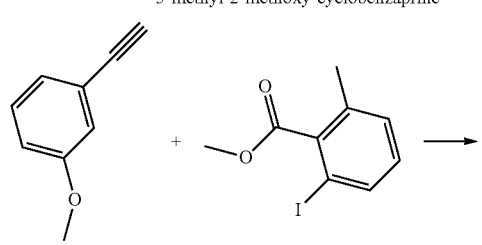

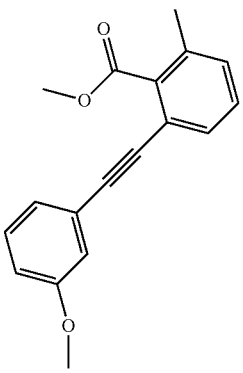

A methyl 2-[2-(3-methoxyphenyl)ethynyl]-6-methylbenzoate [ ]1.2 equivalents of 3-methoxyphenylacetylene are combined with 2-methyl-6-iodobenzoic acid methyl ester in the presence of 3 equivalents of TBAF and 3 mol % PdCl2(PPh3)2 and stirred at 80° C. until the reaction is complete by TLC. (Alternately, 2-methyl-6-bromobenzoic acid methyl ester may be use in place of 2-methyl-6-iodobenzoic acid methyl ester.) The product is isolated by chromatography on silica gel using hexane-ethyl acetate as a solvent. (Y. Liang, Y.-X. Xie, J.-H. Li, *J. Org. Chem.,* 2006, 71, 379-381.)

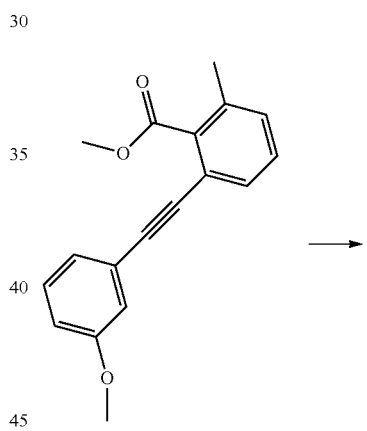

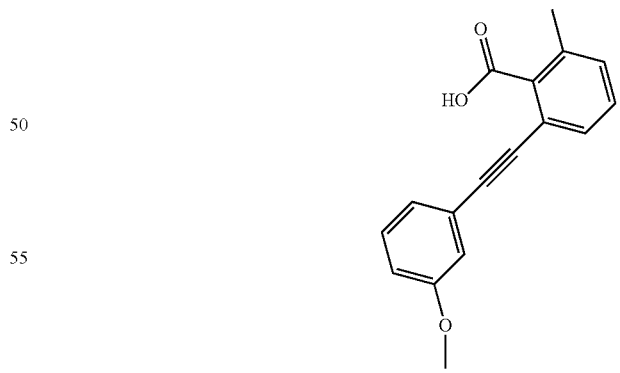

2-[2-(3-methoxyphenyl)ethynyl]-6-methylbenzoic acid The ester is cleaved using 1 equivalent of LiGH in 1:1 H2O/THF. The mixture is stirred at 0° C. for 1 hour, then at 25° C. or 20 hours. The crude product is acidified with HCL, stripped of solvent, dissolved in NaHCO3 aqueous, cooled and acidified to pH 2 to precipitate the product.

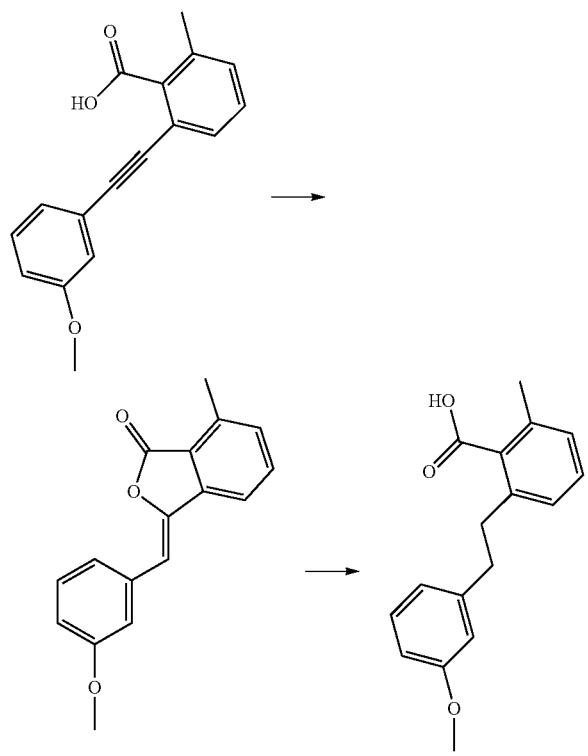

2-[2-(3-methoxyphenyl)ethyl]-6-methylbenzoic acid The acid is converted to intermediate

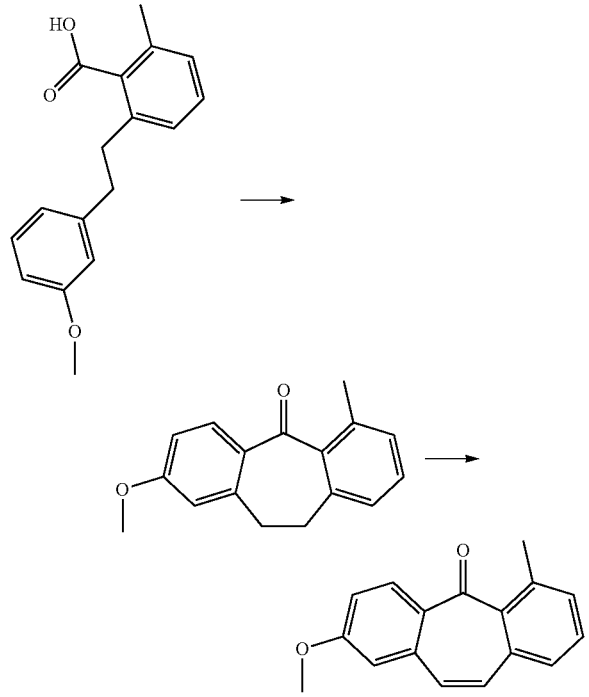

(3Z)-3-[(3-methoxyphenyl)methylidene]-7-methyl-1,3-dihydro-2-benzofuran-1-one with Re(CO)$_5$C$_1$ using the method in Heterocycles V91, pp 2172-9 (2015). This intermediate is purified using SiO2 chromatography and reduced to the final product with Raney nickel and hydrogen according to Noda et al, JOC V59 pp 7968-7975.

2-methoxy-5-methyl dibenzosuberen-11-one

2-[2-(3-methoxyphenyl)ethyl]-6-methylbenzoic acid is cyclized with polyphosphoric acid (PPA) to 2-methoxy-5-methyl dibenzosuberan-11-one. This intermediate is dehydrogenated to the final product by chlorination with NBS in CCl$_4$ followed by triethylamine to remove HCl. The reaction with NBS is followed closely with adjustments in temperature to avoid chlorination of the methyl group Both steps are detailed in Noda et al, JOC V59 pp 7968-7975).

Optionally, as an alternative, 2-methoxy-5-methyl dibenzosuberen-11-one may be made by methylation of 2-methoxy dibenzosuberen-11-one with 0.8 equivalents of trimethylaluminum, catalyzed by Fe(acac)3 (5 mol %) and 4-(bis(2-(diphenylphosphanyl)phenyl)phosphanyl)-N,N-dimethylaniline (NMe2-TP) (5 mol %) in THF under argon, followed by separation of 5-methyl and 4-methyl 2-methoxy dibenzosuberen-11-one by silica chromatography. (Procedure adapted from Shang et al JACS V138 pp 10132-10135 (2016)).

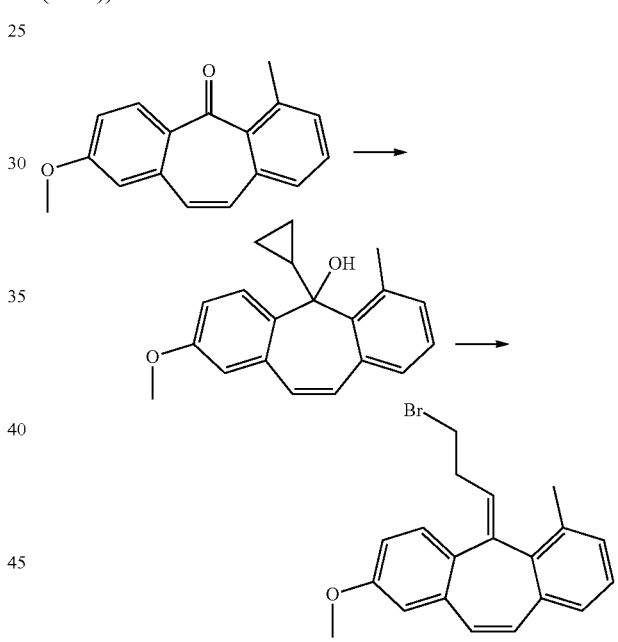

(E)-11-(3-bromopropylidene)-2-methoxy-5-methyldibenzosuberene 2-methoxy-5-methyl dibenzosuberen-11-one is combined with cyclopropylmagnesium bromide in THF to form 2-methoxy-5-methyl 11-cyclopropyl-dibenzosuberene-2-ol: A solution of cyclopropylmagnesium bromide in dry THF (prepared from cyclopropylbromide (8.0 g, 0.067 mol), magnesium turnings (1.3 g, 0.053 mol) and dry THF (35 ml)) is placed under an atmosphere of nitrogen. A solution of 2-methoxy-5-methyl dibenzosuberen-11-on (6.0 g, 0.028 mol) in dry THF (15 ml) is added dropwise and when addition is complete the mixture is heated at reflux for 30 minutes. The reaction mixture is cooled on an ice-bath and saturated ammonium chloride (35 ml) is carefully added. The mixture is diluted with water (50 ml) and extracted with diethyl ether (2×50 ml).

The combined organic extracts are washed with water, dried (Na2 SO4) and the solvent is evaporated in vacuo to give 8.6 g of crude form 2-methoxy-5-methyl 11-cyclopropyl-dibenzosuberene-2-ol. (Novo Nordisk A/S—U.S. Pat. No. 5,595,989). This material is optionally purified by silica chromatography.

The alcohol is converted to the title product with tributylphosphine, CBr4 and DIPEA (Adapted from N. Sakai, T. Maruyama, T. Konakahara, Synlett, 2009, pp 2105-2106). Alternately, concentrated aqueous hydrogen bromide can be used (Novo Nordik A/S—U.S. Pat. No. 5,595,989). (The HBr approach may lead to H/D isotope exchange when certain deuterated analogs are being synthesized.)

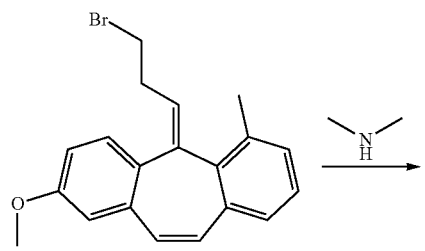

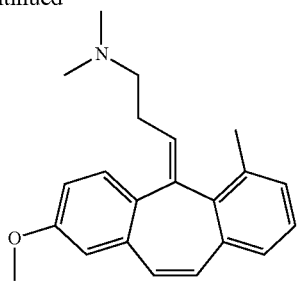

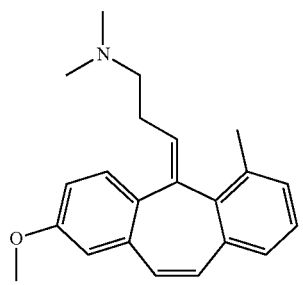

5-methyl-2-methoxy-cyclobenzaprine Dimethylamine hydrochloride (16 mmol), cesium carbonate (6.66 g, 20.45 mmol), and (E)-11-(3-bromopropylidene)-2-methoxy-5-methyldibenzosuberene (5.84 mmol) are suspended in anhydrous acetonitrile (17.6 mL) using a heavy-walled glass reaction vessel which is sealed and stirred at 75° C. for 16 h to give a white suspension. The reaction mixture is cooled to RT, the solids are filtered, washed thrice with acetonitrile, the filtrate is concentrated to give an oil which is partitioned between $Et_2O$ (120 mL) and water (60 mL). The organic layer is washed with brine (60 mL), dried with $MgSO_4$, the solvent is concentrated to give an oil which is further evaporated in vacuo (0.1 mm Hg) for 14 h at RT to give the desired product. Salts with HBr or another acid are formed, and the product can then be recrystallized.

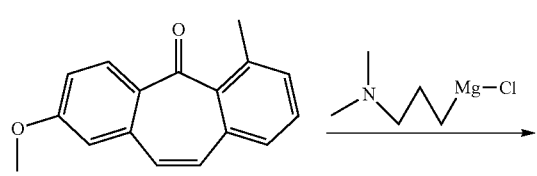

Optionally, the product can be made in a 1 pot procedure from 2-methoxy-5-methyl dibenzosuberen-11-one and dimethylaminopropyl magnesium chloride by adapting a procedure used for cyclobenzaprine (Jain et al, 2011, WO2012098563A2). In a single vessel, 2-methoxy-5-methyl dibenzosuberen-11-one is reacted with dimethylaminopropyl magnesium chloride at a temperature 0-15° C. for 30-90 min. The reaction mass undergoes hydrolysis and dehydration reaction in presence of 15-25% w/v aqueous hydrochloride solution by heating at a temperature about 70-80° C. for 2-3 hrs. After completion of the reaction, the reaction mass is neutralized by using aqueous $Na_2CO_3$ solution and the product is extracted with methylene dichloride. After the complete removal of solvent, the oily mass is dissolved in isopropyl alcohol and the mixture is acidified by slow addition of IPA._HCl solution at 0-10° C. with continuous stirring for 2-3 hrs for complete precipitation. The precipitate is filtered, recrystallized from isopropyl alcohol and dried to obtain the crude product. The product is optionally purified by recrystallization from isopropanol, by silica gel chromatography in a solvent containing 1-3% triethylamine, or both.

Example 10—Preparation of 5-methyl-2-acetoxy-cyclobenzaprine (5-Me-2-AcO-Cbp)

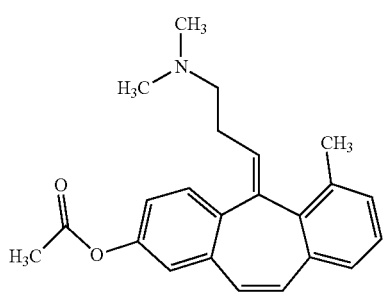 [SMILES: CC(=O)Oc1ccc2c(c1)C=Cc1cccc(C)c1/C2=C/CCN(C)C]

5-methyl-2-hydroxyl-cyclobenzaprine (Example 14) is treated with acetic anhydride in the presence of DIPEA in a polar aprotic solvent such as THF, dioxane or DMF to form the final product. The product is purified either by silica gel chromatography in the presence of 1-3% triethylamine, by reverse phase chromatography on C18 silica, or by recrystallization of the oxalate salt.

Example 11—Preparation of 5-methyl-7-methoxycarbonyl-cyclobenzaprine (5-Me-7-OMe-Cbp)

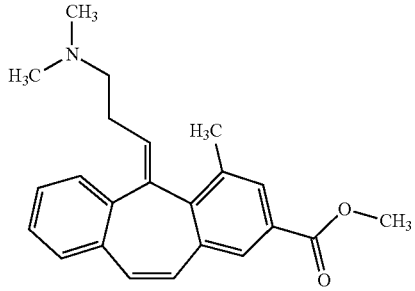 [SMILES: COC(=O)c1cc(C)c2c(c1)C=Cc1ccccc1/C2=C\CCN(C)C]

In a pressure vessel, t-Bu$_2$PCl (0.3 mmoles) and MeOH (20 mL) are stirred for 5 hours at 25° C., atmospheric pressure. 5-methyl-7-bromo-cyclobenzaprine (example 17, 20 mmoles) as the HCl salt and Pd(OAc)$_2$ (0.1 mmoles) are added, and the solution is stirred under 20 bars CO at 115° C. for 18 hours. (Wang et al., Chem Comm V53, pp 7469-7472). The product is purified either by silica gel chromatography in the presence of 1-3% triethylamine, by reverse phase chromatography on C18 silica, or by recrystallization of the oxalate salt.

Example 12—Preparation of 5-methyl-7-methoxy-cyclobenzaprine (5-Me-7-OMe-Cbp)

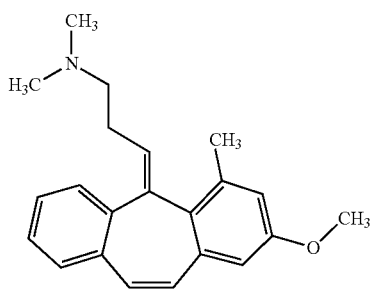 [SMILES: COc1cc(C)c2c(c1)C=Cc1ccccc1/C2=C\CCN(C)C]

The procedure from example 9 is used, replacing 3-methoxyphenylacetylene with phenylacetylene and 2-methyl-6-iodobenzoic acid methyl ester with 2-methyl-4-methoxy-6-iodobenzoic acid methyl ester in the initial step.

Example 13-Preparation of 5-methoxy-cyclobenzaprine (5-MeO-Cpb)

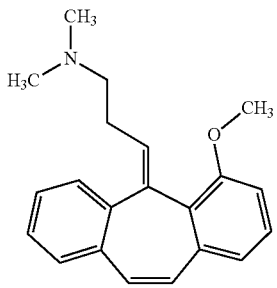 [SMILES: COc1cccc2c1/C(=C/CCN(C)C)c1ccccc1C=C2]

The procedure from example 9 is used, replacing 3-methoxyphenylacetylene with phenylacetylene and 2-methyl-6-iodobenzoic acid methyl ester with 2-methoxy-6-iodobenzoic acid methyl ester in the initial step Example 14—Preparation of 5-methyl-2-hydroxyl-cyclobenzaprine (2-OH-5-Me-Cbp)

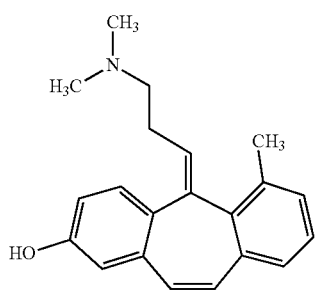 [SMILES: Cc1cccc2c1/C(=C/CCN(C)C)c1ccc(O)cc1C=C2]

5-methyl-2-methoxy-cyclobenzaprine (from Example 9) is selectively 0-demethylated using boron tribromide. Alternately, lithium diphenylphosphide can be used. The crude product is purified as an oxalate salt through recrystallization from a solvent such as isopropanol. Alternately, reverse phase chromatography can be used.

Example 15—Preparation of 5-methyl-2-butoxycarbonyl-cyclobenzaprine (5-Me-7-BuOCO-Cbp)

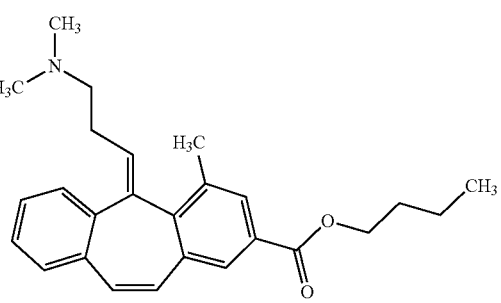

The product is prepared using the procedure in Example 11, using n-butanol instead of methanol.

Example 16: Preparation of 2,7-dimethoxy-cyclobenzaprine (2,7-DiOMe-Cbp)

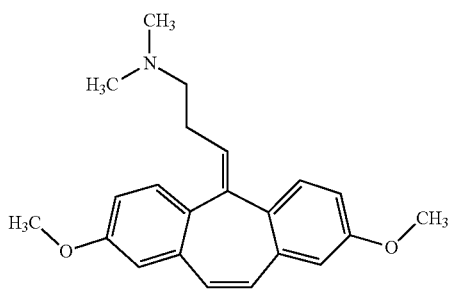

The procedure from example 9 is used, replacing 2-methyl-6-iodobenzoic acid methyl ester with 4-methoxy-2-iodobenzoic acid methyl ester in the initial step.

Example 17: Synthesis of 5-methyl-7-bromo-cyclobenzaprine (5-Me-7-Br-Cbp)

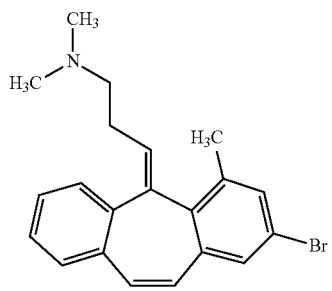 [SMILES: Cc1cc(Br)cc2c1/C(=C/CCN(C)C)c1ccccc1C=C2]

The procedure from example 9 is used, replacing 3-methoxyphenylacetylene with phenylacetylene and 2-methyl-6-iodobenzoic acid methyl ester with 2-methyl-4-bromo-6-iodobenzoic acid methyl ester in the initial Sonogashira coupling step. Conditions are used that lead to selective coupling with the more reaction iodo without reaction at bromo.

Example 18: Synthesis of 1-(3-Dibenzo[a,d]cyclohepten-5-ylidene-propyl)-azetidine (Cbp-Azet1)

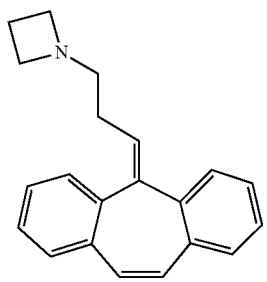 [SMILES: C1=Cc2ccccc2C(=CCCN2CCC2)c2ccccc21]

The procedure from example 4 is used, replacing 3-fluoroazetidine with azetidine. 9,10 dihydro analogs of examples 7, 8, and 18 can be made by starting with 5-(3-bromo-propylidene)-10,11-dihydro-5H-dibenzo[a,d]cycloheptene (synthesis in Novo Nordisk A/S—U.S. Pat. No. 5,595,989) in place of 5-(3-bromo-propylidene) 5H-dibenzo[a,d]cycloheptene. 9,10 dihydro analogs of examples 9-17 can be made by replacing 2-methoxy-5-methyl dibenzosuberen-11-one with 2-methoxy-5-methyl dibenzosuberan-11-one (i.e. by skipping the NCS, triethylamine dehydrogenation step).

What is claimed is:

1. An amitriptyline analog compound of Formula B:

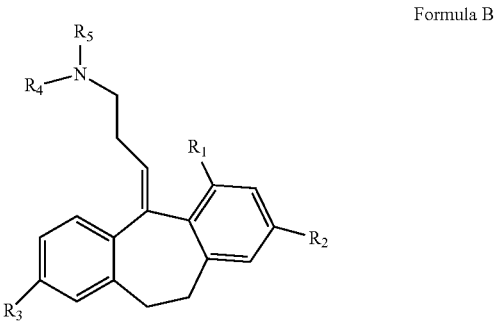

Formula B and pharmaceutically acceptable salts thereof, wherein:

$R_1$ is selected from $C_{1-4}$-alkyl, and $C_{1-4}$-alkoxy;

$R_2$ is selected from H, Br, $(CH_2)_n CO_2 R$ where n=0 to 3 and R=$C_{1-4}$-alkyl, $C_{1-4}$-alkoxy, and halogen;

$R_3$ is selected from H, $C_{1-4}$-alkoxy, OH, and OCOR where R=$C_{1-4}$-alkyl;

$R_4$ is $C_{1-4}$-alkyl wherein if $R_4$ is ethyl the terminus carbon can be optionally substituted by fluorine one to three times; and $R_5$ is $C_{1-4}$-alkyl; or $R_4$ and $R_5$ taken together can form a 4-membered saturated ring optionally substituted with methyl, methoxy, $CF_3$, or $CHF_2$.

2. The compound of claim 1, wherein $R_1$ is $C_{1-4}$-alkyl;

$R_2$ is H;

$R_3$ is $C_{1-4}$-alkoxy;

$R_4$ is $C_{1-4}$-alkyl wherein if $R_4$ is ethyl the terminus carbon can be optionally substituted by fluorine one to three times; and $R_5$ is $C_{1-4}$-alkyl; or $R_4$ and $R_5$ taken together can form a 4-membered saturated ring optionally substituted with methyl, methoxy, $CF_3$, or $CHF_2$.

3. The compound of claim 1, wherein $R_1$ is $C_{1-4}$-alkyl;

$R_2$ is H;

$R_3$ is OCOR where R=$C_{1-4}$-alkyl; $R_4$ is $C_{1-4}$-alkyl wherein if $R_4$ is ethyl the terminus carbon can be optionally substituted by fluorine one to three times; and $R_5$ is $C_{1-4}$-alkyl; or $R_4$ and $R_5$ taken together can form a 4-membered saturated ring optionally substituted with methyl, methoxy, $CF_3$, or $CHF_2$.

4. The compound of claim 1, wherein
$R_1$ is $C_{1-4}$-alkyl;
$R_2$ is $(CH_2)_nCO_2R$ where n=0 and R=methyl;
$R_3$ is H;
$R_4$ is $C_{1-4}$-alkyl wherein if $R_4$ is ethyl the terminus carbon can be optionally substituted by fluorine one to three times; and
$R_5$ is $C_{1-4}$-alkyl; or $R_4$ and $R_5$ taken together can form a 4-membered saturated ring optionally substituted with methyl, methoxy, $CF_3$, or $CHF_2$.

5. The compound of claim 1, wherein
$R_1$ is $C_{1-4}$-alkyl;
$R_2$ is $C_{1-4}$-alkoxy;
$R_3$ is H;
$R_4$ is $C_{1-4}$-alkyl wherein if $R_4$ is ethyl the terminus carbon can be optionally substituted by fluorine one to three times;
$R_5$ is $C_{1-4}$-alkyl; or $R_4$ and $R_5$ taken together can form a 4-membered saturated ring optionally substituted with methyl, methoxy, $CF_3$, or $CHF_2$.

6. The compound of claim 1, wherein,
$R_1$ $C_{1-4}$-alkoxy;
$R_2$ is H;
$R_3$ is H;
$R_4$ is $C_{1-4}$-alkyl wherein if $R_4$ is ethyl the terminus carbon can be optionally substituted by fluorine one to three times; and
$R_5$ is $C_{1-4}$-alkyl; or $R_4$ and $R_5$ taken together can form a 4-membered saturated ring optionally substituted with methyl, methoxy, $CF_3$, or $CHF_2$.

7. The compound of claim 1, wherein
$R_1$ is $C_{1-4}$-alkyl;
$R_2$ is H;
$R_3$ is OH;
$R_4$ is $C_{1-4}$-alkyl; and
$R_5$ is $C_{1-4}$-alkyl.

8. The compound of claim 3, wherein
$R_1$ is $C_{1-4}$-alkyl;
$R_2$ is $(CH_2)_nCO_2R$ where n is 0 and R is $C_{1-4}$-alkyl;
$R_3$ is H;
$R_4$ is $C_{1-4}$-alkyl wherein if $R_4$ is ethyl the terminus carbon can be optionally substituted by fluorine one to three times; and
$R_5$ is $C_{1-4}$-alkyl; or $R_4$ and $R_5$ taken together can form a 4-membered saturated ring optionally substituted with methyl, methoxy, $CF_3$, or $CHF_2$.

9. The compound of claim 1, wherein
$R_1$ is $C_{1-4}$-alkyl;
$R_2$ is Br;
$R_3$ is H;
$R_4$ is $C_{1-4}$-alkyl wherein if $R_4$ is ethyl the terminus carbon can be optionally substituted by fluorine one to three times; and
$R_5$ is $C_{1-4}$-alkyl; or $R_4$ and $R_5$ taken together can form a 4-membered saturated ring optionally substituted with methyl, methoxy, $CF_3$, or $CHF_2$.

10. A amitriptyline analog compound of Formula B,

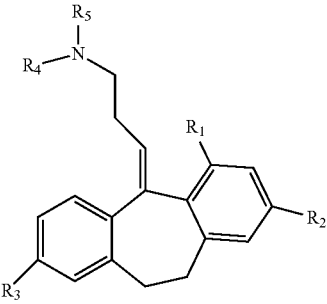

Formula B and pharmaceutically acceptable salts thereof, wherein:
$R_1$ is H;
$R_2$ is selected from H, Br, $(CH_2)_nCO_2R$ where n=0 to 3 and R=$C_{1-4}$-alkyl, $C_{1-4}$-alkoxy, and halogen;
$R_3$ is selected from H, $C_{1-4}$-alkoxy, OH, and OCOR where R=$C_{1-4}$-alkyl;
$R_4$ is methyl or 2,2-difluoroethyl,
$R_5$ is $C_{1-4}$-alkyl; or $R_4$ and $R_5$ taken together can form a 4-membered saturated ring optionally substituted with methyl or methoxy; or $R_4$ and $R_5$ taken together form a 4-membered saturated ring optionally substituted with $CD_3$, $CD_3O$, $CF_3$, or $CDF_2$, and with all other positions substituted with D; wherein the 3 carbons connecting nitrogen to the tricyclic ring system of Formula B are deuterated at all 5 positions ($CDCD_2CD_2$).

11. The compound of claim 10, wherein
$R_1$ is H;
$R_2$ is H;
$R_3$ is H;
$R_4$ is methyl;
and $R_5$ is $C_{1-4}$-alkyl.

12. The compound of claim 10, wherein
$R_1$ is H:
$R_2$ is H;
$R_3$ is H; and
$R_4$ is 2,2-difluoroethyl.

13. The compound of claim 10, wherein
$R_1$ is H;
$R_2$, is H;
$R_3$ is H; and
$R_4$ and $R_5$ taken together form a 4-membered ring that is optionally substituted with Me or OMe.

14. The compound of claim 10, wherein
$R_1$ is H;
$R_2$ is H;
$R_3$ is H;
$R_4$ and $R_5$ are $CD_3$, or $R_4$ and $R_5$ taken together form a 4-membered saturated ring optionally substituted with $CD_3$, $CD_3O$, $CF_3$, or $CDF_2$, and with all other positions substituted with D;
wherein, the 3 carbons connecting nitrogen to the tricyclic ring system of Formula B are deuterated at all 5 positions ($CDCD_2CD_2$).

* * * * *